United States Patent
Okada et al.

(10) Patent No.: US 9,706,920 B2
(45) Date of Patent: Jul. 18, 2017

(54) OPHTHALMOLOGIC APPARATUS

(71) Applicant: KABUSHIKI KAISHA TOPCON, Tokyo (JP)

(72) Inventors: Hiroaki Okada, Saitama (JP); Taisaku Kogawa, Mitaka (JP); Takashi Fujimura, Fujimino (JP); Kohta Fujii, Toda (JP)

(73) Assignee: KABUSHIKI KAISHA TOPCON, Tokyo (JP)

( * ) Notice: Subject to any disclaimer, the term of this patent is extended or adjusted under 35 U.S.C. 154(b) by 48 days.

(21) Appl. No.: 14/651,201

(22) PCT Filed: Dec. 4, 2013

(86) PCT No.: PCT/JP2013/082641
§ 371 (c)(1),
(2) Date: Jun. 10, 2015

(87) PCT Pub. No.: WO2014/091992
PCT Pub. Date: Jun. 19, 2014

(65) Prior Publication Data
US 2015/0313468 A1    Nov. 5, 2015

(30) Foreign Application Priority Data
Dec. 11, 2012    (JP) .................................. 2012-270823

(51) Int. Cl.
*A61B 3/15* (2006.01)
*A61B 3/00* (2006.01)
(Continued)

(52) U.S. Cl.
CPC ............ *A61B 3/152* (2013.01); *A61B 3/0025* (2013.01); *A61B 3/0083* (2013.01); *A61B 3/113* (2013.01);
(Continued)

(58) Field of Classification Search
CPC ....... A61B 3/14; A61B 3/0025; A61B 3/0083; A61B 3/0091; A61B 3/102; A61B 3/11;
(Continued)

(56) References Cited

U.S. PATENT DOCUMENTS

| 6,631,991 B2* | 10/2003 | Wirth | A61L 31/048 351/221 |
| 6,916,096 B2* | 7/2005 | Eberl | A61B 3/12 351/209 |

(Continued)

FOREIGN PATENT DOCUMENTS

| EP | 2138093 A | 12/2009 |
| JP | 58-097340 A | 6/1983 |

(Continued)

OTHER PUBLICATIONS

International Search Report dated Jan. 14, 2014, issued for International Application No. PCT/JP2013/082641.
(Continued)

*Primary Examiner* — William R Alexander
(74) *Attorney, Agent, or Firm* — Procopio, Cory, Gargreaves & Savitch LLP

(57) ABSTRACT

An ophthalmologic apparatus capable of performing suitable examination according to the state of the eye includes an examination optical system used to examine an eye, a drive part, two or more imaging parts, an analyzer, and a controller. The drive part moves the examination optical system. The two or more imaging parts substantially simultaneously photograph the anterior segment of the eye from different directions. The analyzer analyzes photographic images captured by the two or more imaging parts to obtain the three-dimensional position of the eye, and displacement information indicating the displacement direction and displacement amount of the eye due to eye movement. The controller performs a first alignment process of controlling the drive part based on the three-dimensional position to move the examination optical system and a second alignment process of controlling the drive part based on the
(Continued)

displacement information to move the examination optical system.

17 Claims, 18 Drawing Sheets

(51) Int. Cl.
    *A61B 3/113* (2006.01)
    *A61B 3/11* (2006.01)
    *A61B 3/10* (2006.01)
    *A61B 3/117* (2006.01)
    *A61B 3/12* (2006.01)

(52) U.S. Cl.
    CPC .............. *A61B 3/15* (2013.01); *A61B 3/0091* (2013.01); *A61B 3/102* (2013.01); *A61B 3/11* (2013.01); *A61B 3/112* (2013.01); *A61B 3/117* (2013.01); *A61B 3/1225* (2013.01)

(58) Field of Classification Search
    CPC ......... A61B 3/112; A61B 3/113; A61B 3/117; A61B 3/152; A61B 3/1225; A61B 3/15
    USPC ................................. 351/205, 206, 208, 209
    See application file for complete search history.

(56) References Cited

U.S. PATENT DOCUMENTS

| | | | |
|---|---|---|---|
| 8,100,530 B2 * | 1/2012 | Zhou | ........................ G01J 9/00 351/205 |
| 2004/0156019 A1 | 8/2004 | Masaki | |
| 2007/0013867 A1 | 1/2007 | Ichikawa | |
| 2009/0153798 A1 * | 6/2009 | Dick | ...................... A61B 5/021 351/206 |
| 2010/0110172 A1 * | 5/2010 | Satake | ................... A61B 3/102 348/78 |
| 2010/0149489 A1 * | 6/2010 | Kikawa | .................. A61B 3/102 351/206 |
| 2011/0032480 A1 * | 2/2011 | Rathjen | ................ A61B 3/1005 351/206 |
| 2012/0086911 A1 | 4/2012 | Takii et al. | |
| 2015/0085252 A1 * | 3/2015 | Fujimura | .................. A61B 3/15 351/208 |
| 2015/0335234 A1 * | 11/2015 | Okada | .................. A61B 3/0083 351/208 |

FOREIGN PATENT DOCUMENTS

| | | |
|---|---|---|
| JP | 64-058238 A | 3/1989 |
| JP | 2-268730 A | 11/1990 |
| JP | 8-117188 A | 5/1996 |
| JP | 4136690 B | 8/2004 |
| JP | 2006-116090 A | 5/2006 |
| JP | 2008-006103 A | 1/2008 |
| JP | 2009-112664 A | 5/2009 |

OTHER PUBLICATIONS

Partial Supplementary European Search Report for EP App No. 13862633.8 dated Sep. 20, 2016, 7 pgs.

* cited by examiner

| | NORMAL MODE | SMALL PUPIL MODE |
|---|---|---|
| FIXATION LIGHT INTENSITY | a1 | a2 |
| OBSERVATION LIGHT INTENSITY | b1 | b2 |
| IMAGING LIGHT INTENSITY | c1 | c2 |
| DIAPHRAGM | APERTURE I | APERTURE II |
| OPTICAL SYSTEM POSITION | NO SHIFT | SHIFT |

212b

OPHTHALMOLOGIC APPARATUS

The present application is a National Stage entry of PCT/JP2013/082641, filed on Dec. 4, 2013, which claims priority from Japanese Patent Application No. 2012-270823, filed Dec. 11, 2012, the contents of which are incorporated herein by reference in their entirety.

TECHNICAL FIELD

The present invention relates to an ophthalmologic apparatus.

BACKGROUND TECHNOLOGY

Types of ophthalmologic apparatuses include ophthalmologic imaging apparatuses for obtaining images of an eye and ophthalmologic measuring apparatuses for measuring characteristics of an eye.

Examples of ophthalmologic imaging apparatuses include an optical coherence tomography (OCT) apparatus that obtains tomographic images using OCT, a fundus camera that photographs a fundus, a scanning laser ophthalmoscope (SLO) that obtains images of a fundus by laser scanning with a confocal optical system, a slit lamp microscope that obtains images by photographing an optical section of a cornea using slit light, and the like.

Examples of ophthalmologic measuring apparatuses include an eye refractivity examination apparatus (refractometer, keratometer) that measures refractive properties of an eye, a tonometer, a specular microscope that obtains properties of a cornea (cornea thickness, cellular distribution, etc.), a wave-front analyzer that obtains aberration information of an eye using a Shack-Hartmann sensor, and the like.

Regarding ophthalmic examinations using these apparatuses, in terms of precision and accuracy of examinations, position adjustment between the optical system of the apparatus and an eye is very important. This position adjustment is referred to as alignment. Alignment includes the action of aligning the optical axis of the optical system of the apparatus with respect to the axis of an eye (xy alignment), as well as the action of adjusting the distance between the eye and the optical system of the apparatus (z alignment).

[Patent Document 1] Japanese Unexamined Patent Application Publication No. 2009-112664
[Patent Document 2] Japanese Patent No. 4136690

SUMMARY OF THE INVENTION

Problems to be Solved by the Invention

Since the conventional alignment is performed without consideration of the state of the eye, there have been cases that examination cannot be performed properly. For example, when the gaze direction of the eye has been changed as in photographing the periphery of the eye fundus, data may not be obtained as a light flux for fundus examination is blocked by the iris, or flare may be present in an image of the fundus. In addition, the miosis state or eyelid conditions of the eye may also adversely affect the examination.

An objective of the present invention is to provide an ophthalmologic apparatus that is capable of performing suitable examination according to the state of the eye.

Means of Solving the Problems

An ophthalmologic apparatus of an embodiment includes: an examination optical system configured for examining an eye; a drive part configured to move the examination optical system; two or more imaging parts configured to substantially simultaneously photograph an anterior segment of the eye from different directions; an analyzer configured to analyze photographic images captured by the two or more imaging parts to obtain a three-dimensional position of the eye, and displacement information indicating displacement direction and displacement amount of the eye due to eye movement; and a controller configured to perform a first alignment process of controlling the drive part based on the three-dimensional position to move the examination optical system and a second alignment process of controlling the drive part based on the displacement information to move the examination optical system.

Effects of the Invention

According to the present invention, it is possible to suitably perform an examination according to the state of the eye.

DETAILED DESCRIPTION

Embodiments of ophthalmologic apparatuses related to the present invention are explained in detail with reference to the accompanying drawings. Ophthalmologic apparatuses related to the present invention are used for optical examinations of the eye. Such ophthalmologic apparatuses include ophthalmologic imaging apparatuses and ophthalmologic measuring apparatuses as mentioned above. Examples of ophthalmologic imaging apparatuses include an OCT apparatus, a fundus camera, a scanning laser ophthalmoscope, a slit lamp microscope, and the like. Examples of ophthalmologic measuring apparatuses include an eye refractivity examination apparatus, a tonometer, a specular microscope, a wave-front analyzer, and the like. Cases of applying the present invention to an OCT apparatus are explained in the following embodiments; however, the present invention may be applied to any other types of ophthalmologic apparatuses.

In this specification, images obtained by OCT are sometimes referred to as OCT images. Further, a measuring action for forming an OCT image is sometimes referred to as an OCT measurement. Note that the contents of the documents cited in this specification may be employed in the following embodiments.

In the following embodiments, an OCT apparatus using OCT of so-called spectral domain type, in which a low-coherence light source and a spectrometer are included, is described; however, the present invention may also be applied to OCT apparatuses using other types than spectral domain, such as swept source type and enface type. Note that the swept source OCT is a modality of imaging the morphology of an object by: scanning (sweeping) the wavelength of light that is irradiated to the object; acquiring the spectral intensity distribution by successively detecting interference light obtained from superposing the reflected light of the light of each wavelength on reference light; and performing Fourier transform on the acquired spectral intensity distribution. The enface OCT is a modality of irradiating light with a predetermined beam diameter to an object and analyzing the components of interference light obtained from superposing the reflected light thereof on reference light, thereby forming an image of a cross-section of the object perpendicular to the travelling direction of the light, and it is also referred to as full field type.

An apparatus that is configured by combining an OCT apparatus and a fundus camera is explained in the following embodiment; however, the scope in which the present invention is applicable is not limited to such combination apparatuses. The present invention may be applied to an ophthalmologic apparatus with a single function (e.g., a fundus camera).

First Embodiment

Configuration

Figure 1:
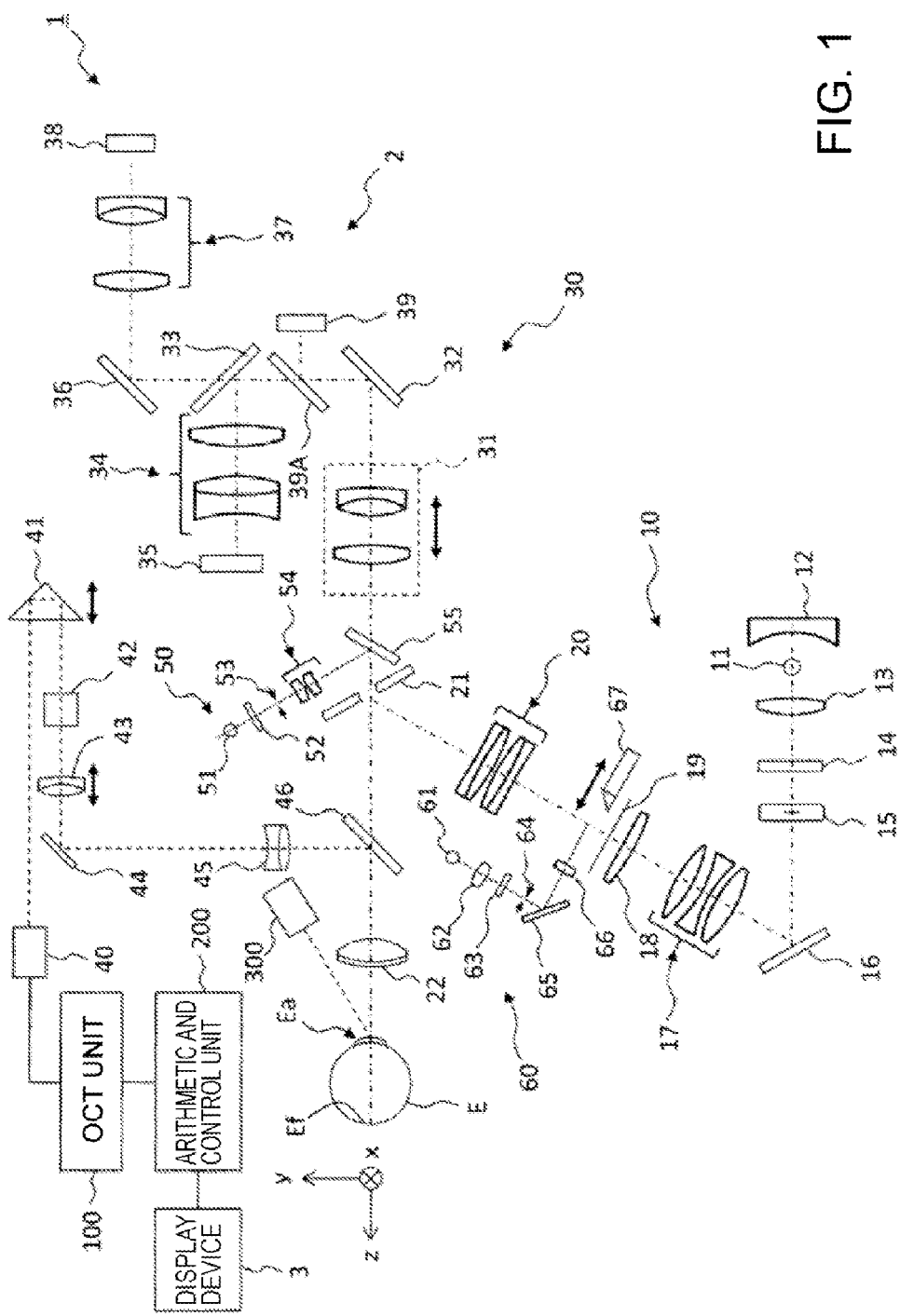
FIG. 1 is a schematic diagram illustrating an example of a configuration of an ophthalmologic apparatus according to an embodiment.

As illustrated in FIG. 1, an ophthalmologic apparatus 1 includes a fundus camera unit 2, an OCT unit 100, and an arithmetic and control unit 200. The fundus camera unit 2 has almost the same optical system as a conventional fundus camera. The OCT unit 100 is provided with an optical system for obtaining an OCT image of a fundus. The arithmetic and control unit 200 is provided with a computer that performs various arithmetic processes, control processes, and the like.

[Fundus Camera Unit]

The fundus camera unit 2 illustrated in FIG. 1 is provided with an optical system for forming a two-dimensional image (fundus image) representing the surface morphology of the fundus Ef of the eye E. Fundus images include observation images, photographic images, and the like. The observation image is, for example, a monochrome moving image formed at a prescribed frame rate using near-infrared light. Note that when the optical system is focused on the anterior eye segment Ea of the eye E, the fundus camera unit 2 may obtain an observation image of the anterior eye segment Ea. The photographic image is, for example, a color image captured by flashing visible light or a monochrome still image using near-infrared light or visible light as illumination light. The fundus camera unit 2 may be configured to be capable of acquiring other types of images such as a fluorescein angiography image, an indocyanine green fluorescent image, and a fundus autofluorescent image.

The fundus camera unit 2 is provided with a jaw holder and a forehead rest for supporting the face of the subject. The jaw holder and the forehead rest correspond to a supporter 440 illustrated in FIGS. 4A and 4B. Note that, in FIGS. 4A and 4B, reference numeral 410 indicates a base that accommodates arithmetic and control circuits and a drive system such as an optical system driver 2A and the like. Reference numeral 420 indicates a case that is located on the base 410 and accommodates optical systems. Reference numeral 430 indicates a lens case that protrudes from the front surface of the case 420 and accommodates an objective lens 22.

The fundus camera unit 2 is provided with an illumination optical system 10 and an imaging optical system 30. The illumination optical system 10 irradiates illumination light to the fundus Ef. The imaging optical system 30 guides the illumination light reflected from the fundus to imaging devices (CCD image sensors 35 and 38, sometimes simply referred to as "CCD"). Moreover, the imaging optical system 30 guides signal light coming from the OCT unit 100 to the fundus Ef, and guides the signal light having passed through the fundus Ef to the OCT unit 100.

An observation light source 11 of the illumination optical system 10 includes, for example, a halogen lamp. The light (observation illumination light) output from the observation light source 11 is reflected by a reflection mirror 12 having a curved reflective surface, and becomes near-infrared after passing through a visible cut filter 14 via a condenser lens 13. Further, the observation illumination light is once converged near an imaging light source 15, reflected by a mirror 16, and passes through relay lenses 17 and 18, an diaphragm 19, and a relay lens 20. Then, the observation illumination light is reflected on the peripheral part (the surrounding region of an aperture part) of an aperture mirror 21, penetrates a dichroic mirror 46, and refracted by the objective lens 22, thereby illuminating the fundus Ef. Note that a light emitting diode (LED) may be used as the observation light source.

The observation illumination light reflected from the fundus is refracted by the objective lens 22, penetrates the dichroic mirror 46, passes through the aperture part formed in the center region of the aperture mirror 21, passes through a dichroic mirror 55, travels through a focusing lens 31, and is reflected by a mirror 32. Further, the fundus reflection light passes through a half mirror 39A, is reflected by a dichroic mirror 33, and forms an image on the light receiving surface of the CCD image sensor 35 by a condenser lens 34. The CCD image sensor 35 detects the fundus reflection light, for example, at a preset frame rate. An image (observation image) based on the fundus reflection light detected by the CCD image sensor 35 is displayed on a display device 3. Note that when the imaging optical system 30 is focused on the anterior eye segment, an observation image of the anterior eye segment Ea of the eye E is displayed. The observation image is an example of a front image obtained by photographing the anterior eye segment Ea from the front of the subject.

The imaging light source 15 is configured, for example, by a xenon lamp. The light (imaging illumination light) output from the imaging light source 15 is irradiated to the fundus Ef via a route as with the observation illumination light. The imaging illumination light reflected from the fundus is guided to the dichroic mirror 33 via the same route as that of the observation illumination light, passes through the dichroic mirror 33, is reflected by a mirror 36, and forms an image on the light receiving surface of the CCD image sensor 38 by a condenser lens 37. An image (photographic image) based on the fundus reflection light detected by the CCD image sensor 38 is displayed on the display device 3. Note that the same device or different devices may be used as the display device 3 for displaying an observation image and the display device 3 for displaying a photographic image. Further, when similar photographing is performed by illuminating the eye E with infrared light, an infrared photographic image is displayed. Moreover, an LED may be used as the imaging light source. The photographic image is an example of a front image obtained by photographing the anterior eye segment Ea from the front of the subject.

A liquid crystal display (LCD) 39 displays a fixation target, a visual target for measuring visual acuity, etc. The fixation target is a visual target for fixating the eye E, and is used during fundus photography and OCT measurement.

Part of the light output from the LCD 39 is reflected by the half mirror 39A, reflected by the mirror 32, travels through the focusing lens 31 and the dichroic mirror 55, passes through the aperture part of the aperture mirror 21, penetrates the dichroic mirror 46, and is refracted by the objective lens 22, thereby being projected onto the fundus Ef.

By changing a display position of the fixation target on the screen of the LCD 39, the projection direction of the fixation target with respect to the eye E, i.e., a fixation position of the eye E, can be changed. Examples of the fixation position of the eye E include, as in conventional fundus cameras, for example, a position for acquiring an image centered on the macula of the fundus Ef, a position for acquiring an image centered on the optic disc, a position for acquiring an image centered on the fundus center between the macula and the optic disc, and the like. Moreover, the display position of the fixation target may be arbitrarily changed.

A method for projecting the fixation target onto the eye E is not limited to this. The fixation position may be changed by, for example, providing an LED group formed of an array of a plurality of LEDs and selectively turning on the LEDs. The fixation position may also be changed by providing one or more movable LEDs.

Further, as with conventional fundus cameras, the fundus camera unit 2 is provided with an alignment optical system 50 and a focus optical system 60. The alignment optical system 50 generates a target (alignment indicator) for position matching (alignment) of the optical system with respect to the eye E. The focus optical system 60 generates a target (split target) for adjusting the focus with respect to the eye E.

The light (alignment light) output from the LED 51 of the alignment optical system 50 travels through diaphragms 52 and 53 and a relay lens 54, is reflected by the dichroic mirror 55, passes through the aperture part of the aperture mirror 21, penetrates the dichroic mirror 46, and is projected onto the cornea of the eye E by the objective lens 22.

The alignment light reflected from the cornea travels through the objective lens 22, the dichroic mirror 46 and the abovementioned aperture part, and part of the cornea reflection light penetrates the dichroic mirror 55, passes through the focusing lens 31, is reflected by the mirror 32, penetrates the half mirror 39A, is reflected by the dichroic mirror 33, and is projected onto the light receiving surface of the CCD image sensor 35 by the condenser lens 34. An image (alignment indicator) captured by the CCD image sensor 35 is displayed on the display device 3 together with the observation image. A user conducts alignment by the same operation as performed on a conventional fundus camera. Instead, alignment may be performed in such a way that the arithmetic and control unit 200 analyzes the position of the alignment indicator to move the optical system (automatic alignment). Note that, in the embodiment, automatic alignment can be performed using anterior eye cameras 300 (described later); therefore, the ability of automatic alignment using the alignment indicator is not necessarily required. However, when automatic alignment using the anterior eye cameras 300 fails, automatic alignment may be performed using an alignment indicator, or automatic alignment using the anterior eye cameras 300 and automatic alignment using the alignment indicator may be selectively used.

To conduct focus adjustment, the reflective surface of a reflection rod 67 is placed aslant in the optical path of the illumination optical system 10. The light (focus light) output from an LED 61 of the focus optical system 60 passes through a relay lens 62, is split into two light fluxes by a split target plate 63, passes through a two-hole diaphragm 64, is reflected by a mirror 65, and is reflected after an image is formed once on the reflective surface of the reflection rod 67 by a condenser lens 66. Further, the focus light travels through the relay lens 20, is reflected by the aperture mirror 21, penetrates the dichroic mirror 46, and is refracted by the objective lens 22, thereby being projected onto the fundus Ef.

The focus light reflected from the fundus passes through the same route as the cornea reflection light of the alignment light and is detected by the CCD image sensor 35. An image (split target) captured by the CCD image sensor 35 is displayed on the display device 3 together with an observation image. As in the conventional case, the arithmetic and control unit 200 analyzes the position of the split target, and moves the focusing lens 31 and the focus optical system 60 for focusing (automatic focusing). The user may perform the focusing manually while visually checking the split target.

The dichroic mirror 46 branches the optical path for OCT measurement from the optical path for fundus photography. The dichroic mirror 46 reflects light of wavelengths used in OCT measurement and transmits light for fundus photography. This optical path for OCT measurement is provided with, in order from the OCT unit 100 side, a collimator lens unit 40, an optical path length changing part 41, a galvano scanner 42, a focusing lens 43, a mirror 44, and a relay lens 45.

The optical path length changing part 41 is movable in the direction indicated by the arrow in FIG. 1, thereby changing the length of the optical path for OCT measurement. This change of the optical path length is used for correcting the optical path length according to the axial length of the eye E, adjusting the interference state, and the like. The optical path length changing part 41 includes, for example, a corner cube and a mechanism for moving it.

The galvano scanner 42 changes the travelling direction of light (signal light LS) travelling through the optical path for OCT measurement. Thereby, the fundus Ef may be scanned with the signal light LS. The galvano scanner 42 includes, for example, a galvano mirror for scanning the signal light LS in the x direction, a galvano mirror for scanning in the y direction, and a mechanism for independently driving them. Accordingly, the signal light LS may be scanned in any direction on the xy plane.

Figure 4A:
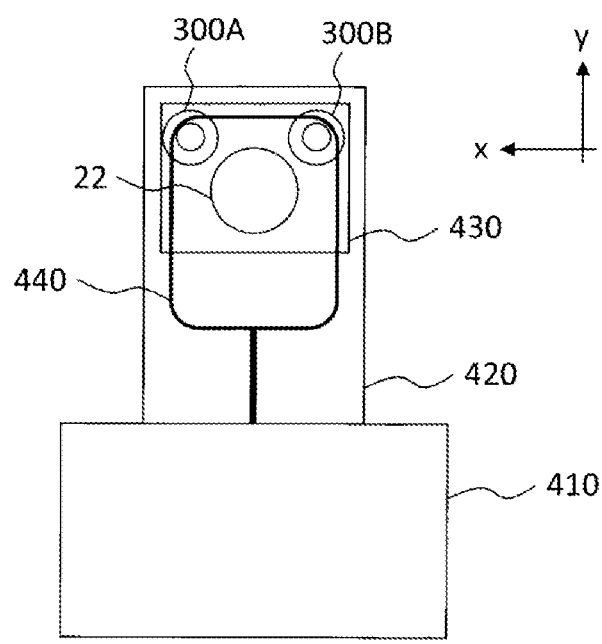
FIG. 4A is a schematic diagram illustrating an example of a configuration of an ophthalmologic apparatus according to an embodiment.
Figure 4B:
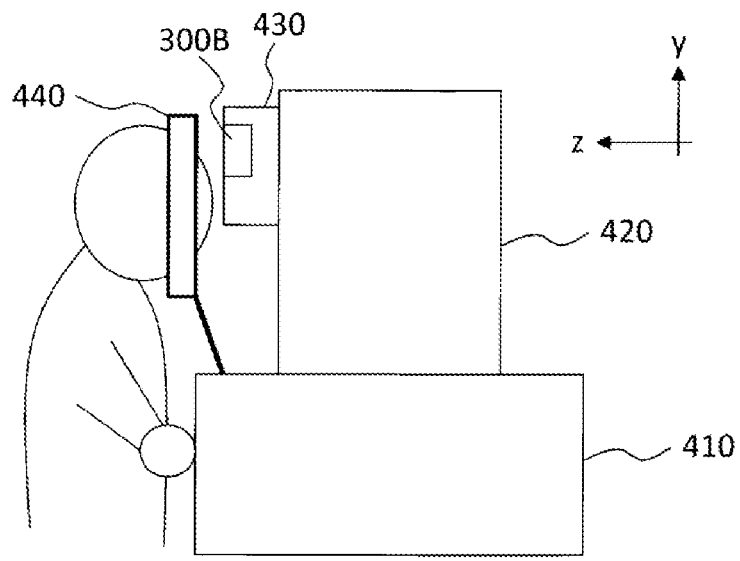
FIG. 4B is a schematic diagram illustrating an example of a configuration of an ophthalmologic apparatus according to an embodiment.

The fundus camera unit 2 is provided with the anterior eye cameras 300. The anterior eye cameras 300 substantially simultaneously photograph an anterior eye segment Ea from different directions. In the embodiment, two cameras are provided on the subject side surface of the fundus camera unit 2 (see anterior eye cameras 300A and 300B in FIG. 4A). Moreover, the anterior eye cameras 300A and 300B are, as illustrated in FIGS. 1 and 4A, arranged in positions away from the optical path of the illumination optical system 10 and the optical path of the imaging optical system 30. The two anterior eye cameras 300A and 300B may be collectively represented by the reference numeral 300.

In the embodiment, while the two anterior eye cameras 300A and 300B are provided, the number of anterior eye cameras may be any number more than one. However, taking into consideration the arithmetic process (described later), it is only required to be capable of substantially simultaneously photographing the anterior eye segment from two different directions. Moreover, in the embodiment, the anterior eye cameras 300 are separately provided from the illumination optical system 10 and the imaging optical system 30; however, similar anterior-eye photography may be performed using at least the imaging optical system 30. That is, one of the two or more anterior eye cameras may include the imaging optical system 30. In any case, in the embodiment, the anterior eye segment may be substantially simultaneously photographed from two (or more) different directions.

Note that "substantially simultaneously" indicates to allow photographing timing deviation of such a degree that eye movement can be ignored in photography using two or more anterior eye cameras. Accordingly, images of the eye E located in substantially the same position (orientation) may be acquired by the two or more anterior eye cameras.

Moreover, photography with the two or more anterior eye cameras may be moving image photography or still image photography; however, in the embodiment, moving image photography is described in detail. In the case of moving image photography, substantially simultaneous photography of the anterior eye segment mentioned above may be realized by controlling the timing to start photography, or controlling frame rates and/or the timing to capture frames. Meanwhile, in the case of still image photography, this may be realized by controlling the timing for photography.

[OCT Unit]

An example of the configuration of the OCT unit 100 is described with reference to FIG. 2. The OCT unit 100 is provided with an optical system for acquiring an OCT image of the fundus Ef. The optical system has a similar configuration to a conventional spectral domain OCT. That is, the optical system is configured to split low-coherence light into reference light and signal light, make the signal light having propagated through a fundus and the reference light having passed through a reference optical path interfere with each other to generate interference light, and detect the spectral components of this interference light. The detection result (detection signal) is sent to the arithmetic and control unit 200.

Note that, in the case of swept source OCT, a wavelength tunable light source is provided instead of a light source that outputs low-coherence light, while an optical element for spectrally decomposing interference light is not provided. Generally, regarding the configuration of the OCT unit 100, known technologies may be applied according to the type of OCT.

A light source unit 101 outputs broadband low-coherence light L0. The low-coherence light L0 includes, for example, near-infrared wavelengths (approximately 800 nm to 900 nm), and has a temporal coherence length of around several tens of micrometers. Note that wavelengths not visible to the human eye, such as near-infrared light with a central wavelength of around 1040 nm to 1060 nm, may be used as the low-coherence light L0.

The light source unit 101 includes a light output device, such as a super luminescent diode (SLD), an LED, a semiconductor optical amplifier (SOA), or the like.

The low coherence light L0 output from the light source unit 101 is guided to a fiber coupler 103 by an optical fiber 102 and split into signal light LS and reference light LR.

The reference light LR is guided by an optical fiber 104 and arrives at an optical attenuator 105. The optical attenuator 105 automatically adjusts the amount of the reference light LR guided by the optical fiber 104 under the control of the arithmetic and control unit 200 using a known technology. The reference light LR whose amount have been adjusted by the optical attenuator 105 is guided by the optical fiber 104 and arrives at a polarization adjuster (polarization controller) 106. The polarization adjuster 106 is a device that, by applying external stress to the looped optical fiber 104, adjusts the polarization condition of the reference light LR guided in the optical fiber 104. Note that the configuration of the polarization adjuster 106 is not limited to this and any known technologies may be used. The reference light LR whose polarization condition has been adjusted by the polarization adjuster 106 arrives at a fiber coupler 109.

The signal light LS generated by the fiber coupler 103 is guided by an optical fiber 107 and collimated into a parallel light flux by the collimator lens unit 40. Further, the signal light LS arrives at the dichroic mirror 46 via the optical path length changing part 41, the galvano scanner 42, the focusing lens 43, the mirror 44, and the relay lens 45. Subsequently, the signal light LS is reflected by the dichroic mirror 46, refracted by the objective lens 22, and projected onto the fundus Ef. The signal light LS is scattered (including reflections) at various depth positions of the fundus Ef. Back-scattered light of the signal light LS from the fundus Ef reversely advances along the same route as the outward path and is guided by the fiber coupler 103, thereby arriving at the fiber coupler 109 via an optical fiber 108.

The fiber coupler 109 causes the back-scattered light of the signal light LS and the reference light LR having passed through the optical fiber 104 to interfere with each other. Interference light LC thus generated is guided by an optical fiber 110 and output from an exit end 111. Further, the interference light LC is converted to a parallel light flux by a collimator lens 112, spectrally divided (spectrally decomposed) by a diffraction grating 113, converged by a convergence lens 114, and projected onto the light receiving surface of a CCD image sensor 115. Note that although the diffraction grating 113 illustrated in FIG. 2 is of transmission type, it is possible to use a spectrally decomposing element of any other type, such as a diffraction grating of reflection type.

The CCD image sensor 115 is, for example, a line sensor, and detects the spectral components of the spectrally decomposed interference light LC and converts the components into electric charges. The CCD image sensor 115 accumulates the electric charges to generate a detection signal, and sends the signal to the arithmetic and control unit 200.

Although a Michelson interferometer is employed in this embodiment, it is possible to employ any type of interferometer such as a Mach-Zehnder-type as appropriate. Instead of a CCD image sensor, other types of image sensor, such as a complementary metal-oxide semiconductor (CMOS) image sensor, may be used.

[Arithmetic and Control Unit]

The configuration of the arithmetic and control unit 200 is described. The arithmetic and control unit 200 analyzes the detection signal fed from the CCD image sensor 115 to form an OCT image of the fundus Ef. An arithmetic process for this is the same as that of a conventional spectral domain OCT.

Further, the arithmetic and control unit 200 controls each part of the fundus camera unit 2, the display device 3, and the OCT unit 100. For example, the arithmetic and control unit 200 displays an OCT image of the fundus Ef on the display device 3.

Moreover, as control of the fundus camera unit 2, the arithmetic and control unit 200 performs: control of action of the observation light source 11, the imaging light source 15 and the LEDs 51 and 61; control of action of the LCD 39; control of movement of the focusing lenses 31 and 43; control of movement of the reflection rod 67; control of movement of the focus optical system 60; control of movement of the optical path length changing part 41; control of action of the galvano scanner 42; control of action of the anterior eye cameras 300; and the like.

Further, as control of the OCT unit 100, the arithmetic and control unit 200 performs: control of action of the light source unit 101; control of action of the optical attenuator 105; control of action of the polarization adjuster 106; control of action of the CCD image sensor 115; and the like.

The arithmetic and control unit 200 includes, for example, a microprocessor, RAM, ROM, a hard disk drive, a communication interface, and the like, as in conventional computers. The storage device such as a hard disk drive stores computer programs for controlling the ophthalmologic apparatus 1. The arithmetic and control unit 200 may be provided with various types of circuit boards, such as a circuit board for forming OCT images. The arithmetic and control unit 200 may further include an operation device (input device) such as a keyboard and a mouse, and a display device such as LCD.

The fundus camera unit 2, the display device 3, the OCT unit 100, and the arithmetic and control unit 200 may be integrally provided (i.e., in a single case), or they may be distributed to two or more cases.

[Control System]

Figure 3:
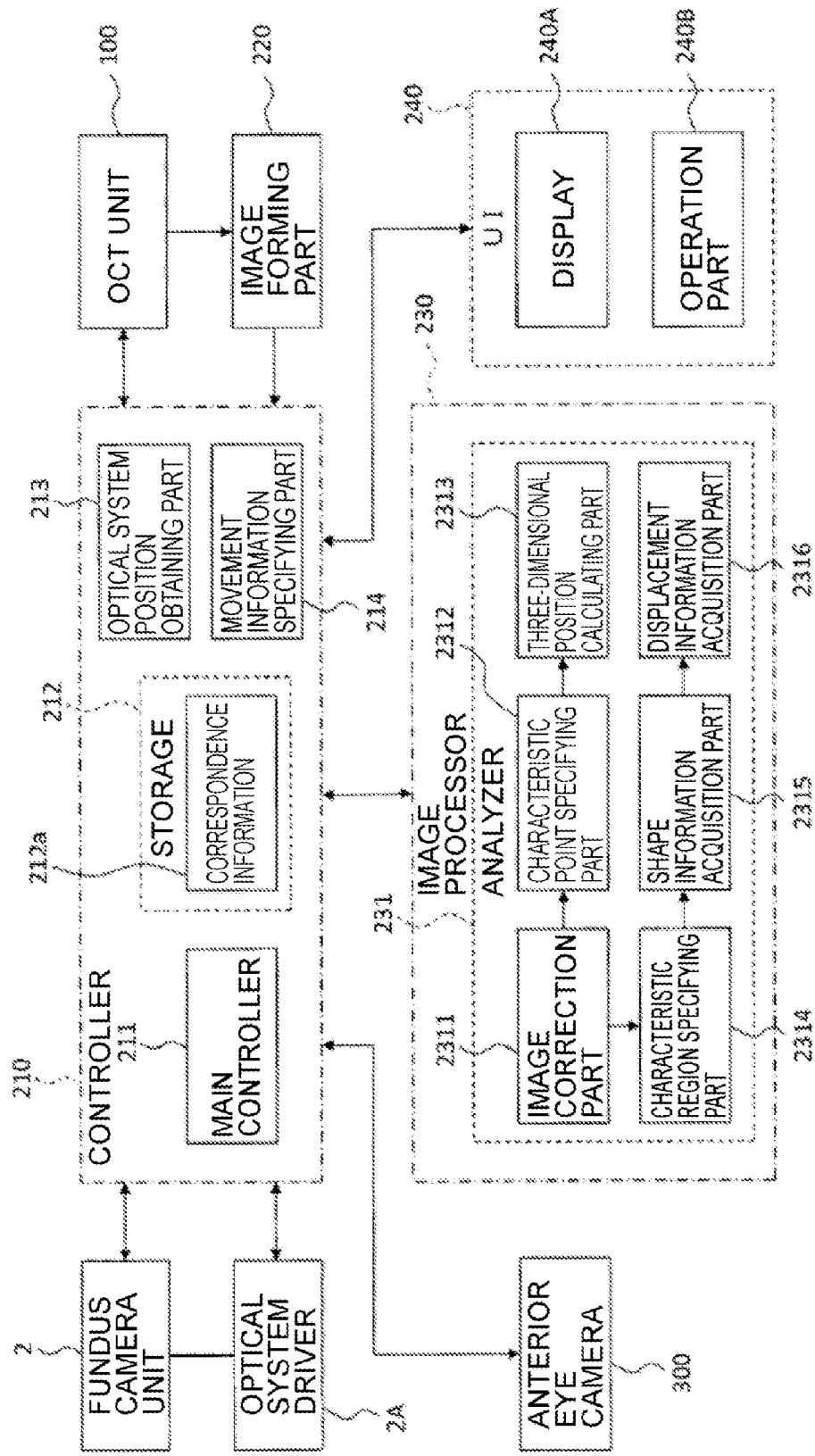
FIG. 3 is a schematic diagram illustrating an example of a configuration of an ophthalmologic apparatus according to an embodiment.

The configuration of a control system of the ophthalmologic apparatus 1 is described with reference to FIG. 3.

(Controller)

The control system of the ophthalmologic apparatus 1 is configured with a controller 210 as a center. The controller 210 includes, for example, the aforementioned microprocessor, RAM, ROM, a hard disk drive, and a communication interface, etc. The controller 210 is provided with a main controller 211, a storage 212, an optical system position obtaining part 213, and a movement information specifying part 214.

(Main Controller)

The main controller 211 performs various types of controls mentioned above. Note that the movement control of the focusing lens 31 is to control a focus driver (not illustrated) to move the focusing lens 31 in the optical axis direction. This changes the focusing position of the imaging optical system 30. The main controller 211 is capable of controlling the optical system driver 2A to three-dimensionally move the optical system installed in the fundus camera unit 2.

This control is implemented by automatic alignment and/or tracking. Here, tracking is to move the optical system of the apparatus according to the eye movement of the eye E. Tracking is performed at, for example, the stage after alignment (focusing is also performed in advance in some cases). Tracking is a function of maintaining a suitable positional relationship in which alignment (and focus) is matched by causing the position of the optical system of the apparatus to follow the eye movement.

Note that the optical system driver 2A of the embodiment moves the optical system installed in the fundus camera unit 2; however, the optical system driver 2A may be configured to move the optical system installed in the OCT unit 100 as well as the optical system installed in the fundus camera unit 2. The optical system driver 2A is an example of "drive part".

The anterior eye cameras 300 of the embodiment are provided on the case of the fundus camera unit 2, and therefore can be moved by controlling the optical system driver 2A. Moreover, it is possible to provide a photography moving part that is capable of independently moving the two or more anterior eye cameras 300. Specifically, the photography moving part may include a driving mechanism (actuator, power transmission mechanism, etc.) provided with respect to each of the anterior eye cameras 300. The photography moving part may also be configured to move the two or more anterior eye cameras 300 by transmitting power generated by a single actuator through a power transmission mechanism of each of the anterior eye cameras 300.

The main controller 211 performs a process of writing data into the storage 212, and a process of reading out data from the storage 212.

(Storage)

The storage 212 stores various types of data. Examples of the data stored in the storage 212 include, for example, image data of an OCT image, image data of a fundus image, and eye information. The eye information includes information related to a subject such as patient ID and name, information related to the subject's eye such as identification information of left eye/right eye, and the like. The storage 212 further stores various types of programs and data to run the ophthalmologic apparatus 1.

Specifically, the storage 212 stores aberration information (not illustrated) in advance. The aberration information includes, for each of the anterior eye cameras 300, information regarding distortion aberration occurred in a photographic image due to effects of the optical system installed therein. Here, the optical system installed in the anterior eye cameras 300 includes, for example, an optical element that causes distortion aberration of the lens or the like. The aberration information can be referred to as a parameter that quantifies the deformation of a photographic image caused by such optical elements.

An example of a method for generating the aberration information is explained. Taking into account instrumental error (difference in distortion aberration) of the anterior eye cameras 300, the following measurements are performed for each of the anterior eye cameras 300. An operator prepares a specific reference point. The reference point is a photographing target used in detecting the distortion aberration. The operator performs photography multiple times while changing the relative position between the reference point and each of the anterior eye cameras 300. With this, a plurality of photographic images of the reference point photographed from different directions is obtained. The operator analyzes the acquired photographic images using a computer to generate the aberration information of the anterior eye camera 300. Note that the computer that performs this analysis process may be an image processor 230 or any other computer (computer for inspection before shipping products, computer for maintenance, etc.).

The analysis process for generating the aberration information includes, for example, the following steps:

an extraction step for extracting an image region corresponding to the reference point in each photographic image;

a distribution state calculating step for calculating the distribution state (coordinates) of the image region corresponding to the reference point in each photographic image;

a distortion aberration calculating step for calculating a parameter indicating distortion aberration based on the obtained distribution state; and a correction factor calculating step for calculating a factor for correcting the distortion aberration based on the obtained parameter.

Note that the parameter related to the distortion aberration that the optical system gives to an image may include the principal distance, the position of a principal point (in vertical and horizontal directions), the distortion of a lens (in radiation direction and tangential direction), and the like. The aberration information is constructed as information (e.g., table information) that associates the identification information of each of the anterior eye cameras 300 and the correction factor corresponding thereto. The main controller 211 stores the aberration information generated in this manner in the storage 212. The generation of such aberration information and the aberration correction based on this are referred to as camera calibration or the like.

The storage 212 also stores correspondence information 212a in advance. In the correspondence information 212a, movement directions and movement amounts of the examination optical system are associated with displacement directions and displacement amounts of the eye. The displacement directions and the displacement amounts of the eye indicate displacements of the eye due to eye movement (details are described later). Examples of the eye movement include, horizontal movement, up and down (vertical) movement, cycloduction, etc.

In this embodiment, for example, in the examination of the eye affected by eye movement as in the case of examining the periphery of the fundus, the position of the examination optical system is adjusted according to the state of the eye movement. The correspondence information 212a associates states of the eye movement (i.e., displacement directions and displacement amounts of the eye) with movement contents of the examination optical system (movement direction and movement amount). The movement directions are directions perpendicular to the optical axis of the examination optical system. In other words, the movement directions are any direction in the xy plane illustrated in FIG. 1.

The correspondence information 212a is created by simulation, for example. As an example of this simulation, ray tracing can be performed while the displacement direction and the displacement amount of a model eye are being changed. The displacement direction is set equal to the displacement direction of the model eye. The displacement amount is set by the simulation.

When the position of the examination optical system is adjusted according to the state of eye movement, there may be a change of the optical distance between the examination position and the incident position where the light for examination is incident on the eye. For example, in the examination of the central portion of the fundus, the light for examination is incident on the eye from the vicinity of the corneal apex and is irradiated to the central portion of the fundus. On the other hand, in the examination of the peripheral portion, the light for examination is incident on the eye from the periphery of the cornea or the sclera and is irradiated to the peripheral portion of the fundus. Besides, the incident position on the crystalline lens also affects the optical distance of the light for examination. Since the ocular optical system is configured to be substantially rotationally symmetrical with respect to the axis of the eye ball, the change of the optical distance is mainly affected by the amount of movement of the examination optical system. In consideration of this situation, the change of the optical distance corresponding to the movement amount of the examination optical system may be determined by simulation or the like as the movement amount of the examination optical system in the optical axis direction (z direction). This movement amount is recorded in the correspondence information 212a as, for example, a correction amount for a predetermined working distance. Here, the working distance is a preset value indicating the distance between the examination optical system and the eye during the examination using the examination optical system.

The displacement direction of the examination optical system may include the cycloduction direction of the eye E, and the displacement amount may include the cycloduction amount of the eye E. In that case, the correspondence information 212a associates the movement direction and the movement amount with the cycloduction direction and the cycloduction amount. Such correspondence relationship is obtained by, for example, simulation similar to the above.

(Optical System Position Obtaining Part)

The optical system position obtaining part 213 obtains the current position of the examination optical system installed in the ophthalmologic apparatus 1. The examination optical system is an optical system used for optically examining the eye E. The examination optical system in the ophthalmologic apparatus 1 of the embodiment (combined machine of a fundus camera and an OCT apparatus) is an optical system for obtaining images of an eye.

The optical system position obtaining part 213 receives information representing the content of the movement control of the optical system driver 2A by the main controller 211, and obtains the current position of the examination optical system moved by the optical system driver 2A. A specific example of this process is explained. The main controller 211 controls the optical system driver 2A at a predetermined timing (upon start-up of the apparatus, upon inputting patient information, etc.) and moves the examination optical system to a predetermined initial position. Thereafter, the main controller 211 records the control content each time the optical system driver 2A is controlled. Thereby, a history of the control contents may be obtained. The optical system position obtaining part 213 refers to this history and obtains the control contents up to the present time, and determines the current position of the examination optical system based on the control contents.

Alternatively, each time controlling the optical system driver 2A, the main controller 211 may send the control content thereof to the optical system position obtaining part 213 so that the optical system position obtaining part 213 can determine the current position of the examination optical system each time it receives the control content.

For another example, the optical system position obtaining part 213 may be provided with a position sensor that detects the position of the examination optical system.

When the current position of the examination optical system is obtained by the optical system position obtaining part 213 as described above, the main controller 211 can control the optical system driver 2A to move the examination optical system based on the obtained current position and the three-dimensional position of the eye E obtained by an analyzer 231 (described later). Specifically, the main controller 211 recognizes the current position of the examination optical system from the result obtained by the optical system position obtaining part 213, and recognizes the three-dimensional position of the eye E from the analysis result of the analyzer 231. Subsequently, to bring the position of the examination optical system with respect to the three-dimensional position of the eye E in a predetermined positional relationship, the main controller 211 changes the position thereof with the current position of the examination optical system as a starting point. This predetermined positional relationship indicates that the positions in the x and y directions match each other, while the distance in the z direction is a predetermined working distance.

(Movement Information Specifying Part)

As described in detail later, the analyzer 231 analyzes a photographic image captured by the anterior eye cameras 300 and thereby obtains displacement information indicating the displacement direction and the displacement amount of the eye E due to eye movement. The movement information specifying part 214 specifies the movement direction and the movement amount corresponding to the displacement direction and the displacement amount indicated by the displacement information based on the correspondence information 212a. In this process, the movement direction and the movement amount associated with the displacement direction and the displacement amount indicated by the displacement information are searched for from the correspondence relationship contained in the correspondence information 212a.

(Image Forming Part)

An image forming part 220 forms image data of a tomographic image of the fundus Ef based on a detection signal from the CCD image sensor 115. As with a conventional spectral domain OCT, this process includes noise removal (noise reduction), filtering, fast Fourier transform (FFT), and the like. In the case of another type of OCT apparatus, the image forming part 220 performs known processes according to the type thereof.

The image forming part 220 includes, for example, the aforementioned circuit boards. Note that "image data" and the "image" based thereon may be treated in the same way in this specification.

(Image Processor)

The image processor 230 performs various types of image processing and analysis on an image formed by the image forming part 220. For example, the image processor 230 performs various correction processes such as luminance correction and dispersion compensation of the image. Further, the image processor 230 performs various types of image processing and analysis on an image (fundus image, anterior eye image, etc.) obtained by the fundus camera unit 2.

The image processor 230 performs known image processing such as an interpolation process for interpolating pixels between tomographic images, thereby forming image data of a three-dimensional image of the fundus Ef. The image data of a three-dimensional image refers to image data in which the positions of pixels are defined by the three-dimensional coordinates. Examples of the image data of a three-dimensional image include image data composed of three-dimensional arrays of voxels. This image data is referred to as volume data, voxel data, or the like. For displaying an image based on the volume data, the image processor 230 performs a rendering process (such as volume rendering, maximum intensity projection (MIP), etc.) on the volume data to form image data of a pseudo three-dimensional image taken from a specific view direction. This pseudo three-dimensional image is displayed on a display 240A.

Further, stack data of multiple tomographic images may be formed as the image data of a three-dimensional image. The stack data is image data obtained by three-dimensionally arranging the multiple tomographic images obtained along multiple scanning lines, based on the positional relationship of the scanning lines. That is, the stack data is image data obtained by expressing the multiple tomographic images originally defined by individual two-dimensional coordinate systems by a three-dimensional coordinate system (namely, embedding the images in a three-dimensional space).

(Analyzer)

The image processor 230 is provided with the analyzer 231. The analyzer 231 analyzes two photographic images captured substantially simultaneously by the anterior eye cameras 300A and 300B, thereby obtaining the three-dimensional position of the eye E. As an example of a configuration for performing this process, the analyzer 231 is provided with an image correction part 2311, a characteristic point specifying part 2312, and a three-dimensional position calculating part 2313.

In addition, the analyzer 231 analyzes a photographic image captured by the anterior eye cameras 300 and thereby obtains displacement information indicating the displacement direction and the displacement amount of the eye E due to eye movement. As an example of a configuration for performing this process, the analyzer 231 is provided with a characteristic region specifying part 2314, a shape information acquisition part 2315, and a displacement information acquisition part 2316.

(Image Correction Part)

The image correction part 2311 corrects distortion of each photographic image captured by the anterior eye cameras 300 based on the aberration information stored in the storage 212. This process may be performed by, for example, known image processing technology based on a correction factor for correcting distortion aberration. Note that, if the distortion aberration caused in a photographic image due to the optical system of the anterior eye cameras 300 is sufficiently small or the like, the aberration information and the image correction part 2311 are not necessary.

(Characteristic Point Specifying Part)

The characteristic point specifying part 2312 analyzes each photographic image (with its distortion aberration corrected by the image correction part 2311), thereby specifying a position in the photographic image corresponding to a predetermined characteristic point of the anterior eye segment Ea (referred to as "characteristic point"). As the predetermined characteristic point, for example, the center of the pupil or the corneal apex of the eye E may be used. In the following, a specific example of a process for specifying the center of the pupil is explained.

First, the characteristic point specifying part 2312 specifies an image region (pupil region) corresponding to the pupil of the eye E based on the distribution of pixel values (luminance values etc.) in a photographic image. Generally, the pupil is represented with lower luminance compared to other parts, and therefore, the pupil region may be specified by searching an image region with low luminance. At this time, the pupil region may be specified by taking the shape of the pupil into consideration. That is, the pupil region may be specified by searching for a substantially circular image region with low luminance.

Next, the characteristic point specifying part 2312 specifies the center position of the specified pupil region. As mentioned above, the pupil is substantially circular. Accordingly, by specifying the contour of the pupil region and then specifying the center position of an ellipse approximating this contour, this may be used as the center of the pupil. Instead, by deriving the center of the gravity of the pupil region, this center of the gravity may be used as the center of the pupil.

Note that, even when other characteristic points are employed, the position of the characteristic point may be specified based on the distribution of pixel values in a photographic image in the same manner as mentioned above.

(Three-Dimensional Position Calculating Part)

The three-dimensional position calculating part 2313 calculates the three-dimensional position of the characteristic point of the eye E based on the positions of the two or more anterior eye cameras 300 and the positions of characteristic points specified by the characteristic point specifying part 2312 in two or more photographic images. This process is explained with reference to FIGS. 5A and 5B.

Figure 5A:
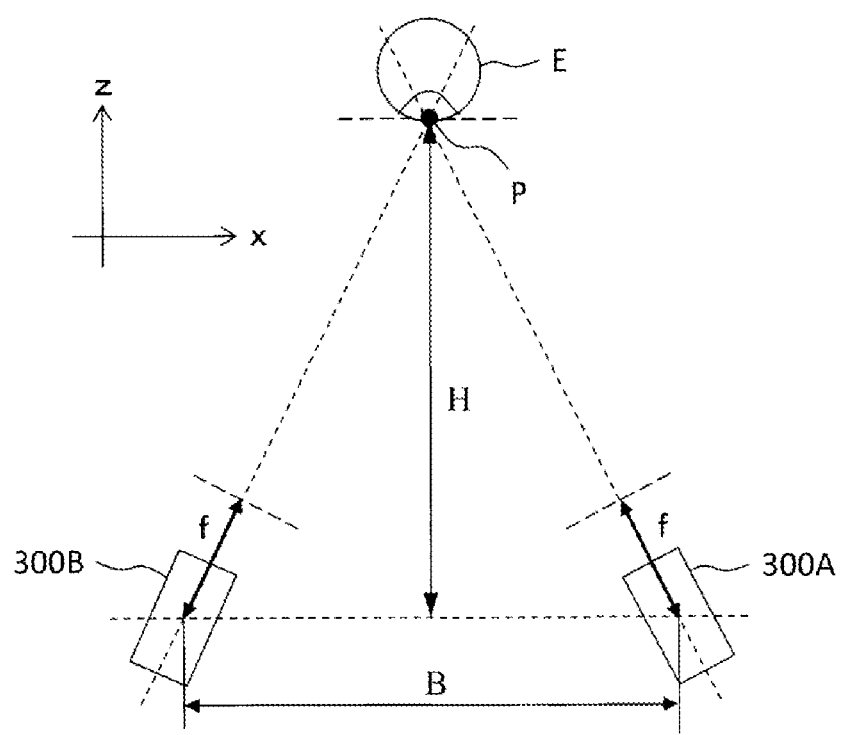
FIG. 5A is a schematic diagram for explaining processing performed by an ophthalmologic apparatus according to an embodiment.
Figure 5B:
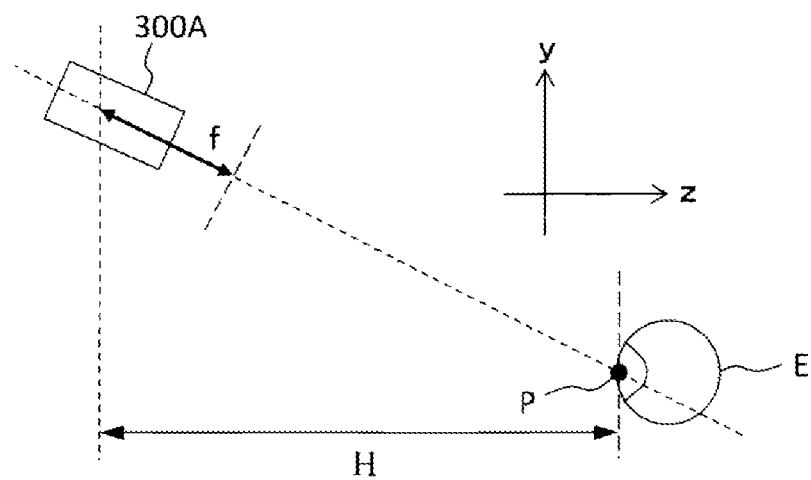
FIG. 5B is a schematic diagram for explaining processing performed by an ophthalmologic apparatus according to an embodiment.

FIG. 5A is a top view illustrating the positional relationship between the eye E and the anterior eye cameras 300A and 300B. FIG. 5B is a side view illustrating the positional relationship between the eye E and the anterior eye cameras 300A and 300B. The distance (base line length) between the two anterior eye cameras 300A and 300B is represented as "B". The distance (photographing distance) between the base line of the two anterior eye cameras 300A and 300B and a characteristic site P of the eye E is represented as "H". The distance (screen distance) between the anterior eye cameras 300A and 300B and the screen plane is represented as "f".

In such an arrangement state, the resolution of images photographed by the anterior eye cameras 300A and 300B is expressed by the following formula, where $\Delta p$ represents the pixel resolution:

$xy$ resolution (planar resolution): $\Delta xy = H \times \Delta p / f$ $z$ resolution (depth resolution): $\Delta z = H \times H \times \Delta p / (B \times f)$ The three-dimensional position calculating part 2313 applies known trigonometry, taking into account the positional relationship illustrated in FIGS. 5A and 5B, to the positions of the two anterior eye cameras 300A and 300B (these are known) and positions corresponding to the characteristic site P in two photographic images, thereby calculating the three-dimensional position of the characteristic site P, that is, the three-dimensional position of the eye E.

The three-dimensional position of the eye E calculated by the three-dimensional position calculating part 2313 is sent to the controller 210. Based on this calculation result of the three-dimensional position, the controller 210 controls the optical system driver 2A such that the optical axis of the examination optical system matches the axis of the eye E, and that the distance from the eye E to the examination optical system becomes a predetermined working distance.

When the anterior eye cameras 300 acquire moving images of the anterior eye segment Ea in parallel from different directions, tracking of the examination optical system may be performed with respect to the movement of the eye E by performing, for example, the following processes (1) and (2):

(1) The analyzer 231 successively analyzes two or more frames captured substantially simultaneously by acquiring moving images with the two or more anterior eye cameras 300, thereby successively obtaining the three-dimensional position of the eye E.

(2) The controller 210 successively controls the optical system driver 2A based on the three-dimensional position of the eye E successively obtained by the analyzer 231, thereby causing the position of the examination optical system to follow the movement of the eye E.

(Characteristic Region Specifying Part)

The characteristic region specifying part 2314 analyzes a photographic image captured by the anterior eye cameras 300, and thereby specifies a characteristic region in the photographic image corresponding to the characteristic site of the anterior eye segment Ea. This process can be performed in the same manner as the characteristic point specifying part 2312 does. Examples of the characteristic site of the anterior eye segment Ea include the pupil and the iris. The characteristic region corresponding to the pupil is referred to as a "pupil region", and the characteristic region corresponding to the iris is referred to as an "iris region".

The characteristic region specifying part 2314 may analyze a photographic image to which the image correction part 2311 has applied the above correction. When a target of the characteristic point specifying part 2312 and that of the characteristic region specifying part 2314 are the same site of the anterior eye segment Ea (e.g., when the both are the pupil), processing of the characteristic region specifying part 2314 is included in processing of the characteristic point specifying part 2312. Therefore, the characteristic region specifying part 2314 is not necessary. In that case, the shape information acquisition part 2315 is fed with information on a characteristic region specified by the characteristic point specifying part 2312.

(Shape Information Acquisition Part)

In the examination of the eye affected by eye movement as in the case of examining the periphery of the fundus, the shape of the characteristic region (pupil, etc.) of the anterior eye segment Ea varies in the photographic image according to the displacement direction and the displacement amount of the eye E. The shape information acquisition part 2315 acquires the shape of such characteristic region.

The shape information acquisition part 2315 analyzes a characteristic region specified by the characteristic region specifying part 2314, and thereby acquires the shape information of the characteristic region. An example of this process is described. The shape information acquisition part 2315, first, finds an ellipse approximating the contour of the characteristic region (the pupil region, the iris region, etc.). This process can be performed in the same manner as the characteristic point specifying part 2312 does, for example.

The shape information acquisition part 2315 calculates the major axis and the minor axis of the approximate ellipse. This process is performed, for example, in the following manner. First, the shape information acquisition part 2315 finds straight lines of various orientations (inclinations) passing through the center of the approximated ellipse, and then specifies a first straight line with the longest segment contained inside the approximated ellipse and a second straight line with the shortest segment. Further, the shape information acquisition part 2315 sets the length of the above segment in the first straight line as the major axis, and the length of the above segment in the second straight line as the minor axis. Here, the length of the segment is calculated as a distance defined in the photographic image (e.g., the number of pixels), or as a distance in terms of the real space. The shape information of this embodiment includes information of the major axis and the minor axis acquired. Note that the shape information is not limited thereto.

(Displacement Information Acquisition Part)

The displacement information acquisition part 2316 acquires the displacement information indicating the displacement direction and the displacement amount of the eye E due to eye movement based on the shape information acquired by the shape information acquisition part 2315. This process is performed with reference to, for example, information created in advance, which associates information indicated by the shape information with the displacement direction and the displacement amount. This information is referred to as "shape/displacement correspondence information". The shape/displacement correspondence information is created by, for example, obtaining the directions of the major axis and the minor axis and the ratio between them (ellipticity) corresponding to various orientations of the eye or a model eye by means of simulation or actual measurement.

(Process Related to Alignment with Indicator)

Figure 6A:
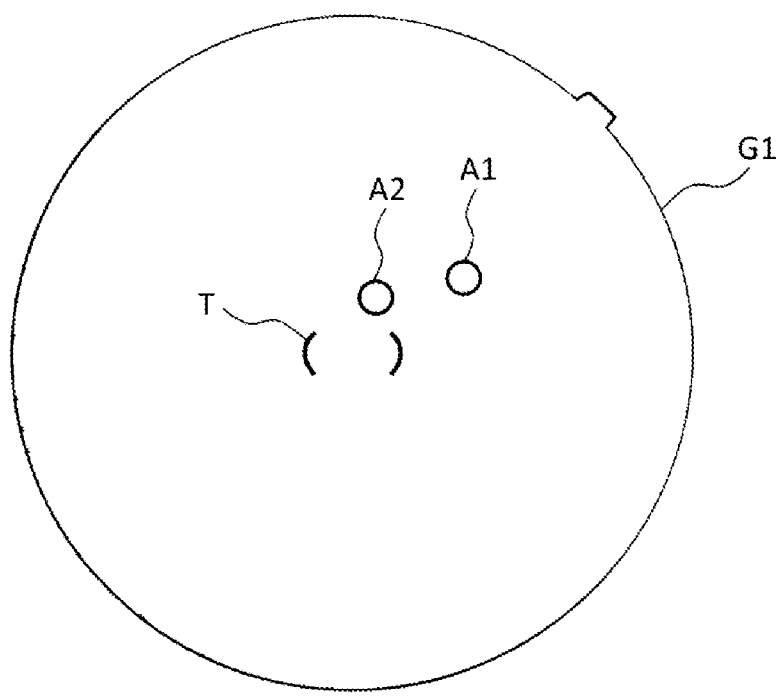
FIG. 6A is a schematic diagram for explaining processing performed by an ophthalmologic apparatus according to an embodiment.
Figure 6B:
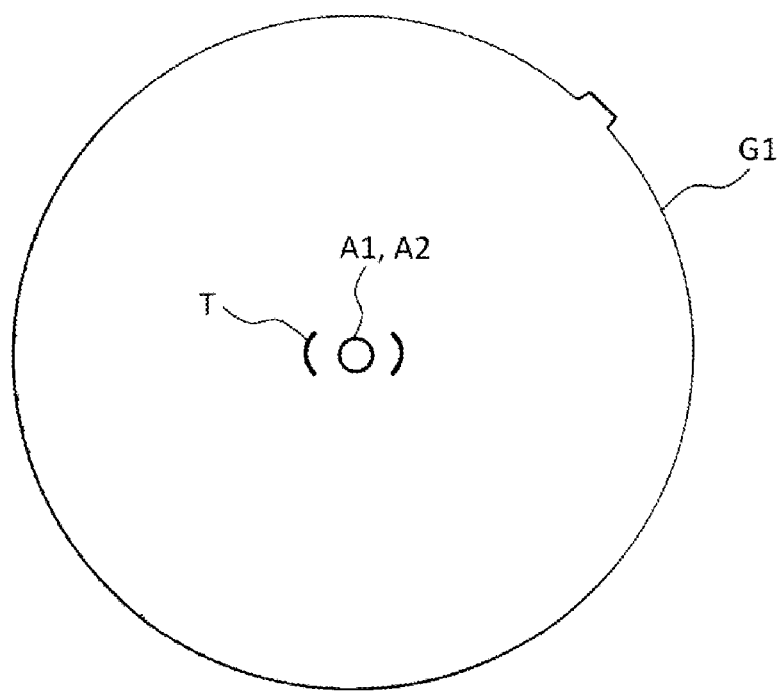
FIG. 6B is a schematic diagram for explaining processing performed by an ophthalmologic apparatus according to an embodiment.

Described below is an example of a process that is performed by the analyzer 231 when the alignment is applied. For the alignment, a front image (e.g., an observation image) of the anterior eye segment Ea acquired by the illumination optical system 10 and the imaging optical system 30 is obtained. The front image is obtained by photographing the anterior eye segment Ea on which the alignment indicator is being projected. Accordingly, the alignment indicator is depicted in the front image. FIGS. 6A and 6B illustrate examples of how the alignment indicator is depicted. In FIGS. 6A and 6B, the image of the eye E is omitted.

In the front image G1 of the eye E illustrated in FIG. 6A, two images (alignment indicator images) A1 and A2 of the alignment indicator are each depicted as a bright spot. The main controller 211 displays a bracket-shaped target image T, which indicates the target position of the alignment, to be superimposed on the center of the front image G1.

If the alignment with respect to the eye E is shifted in the xy directions, the alignment indicator images A1 and A2 are rendered at positions away from the target image T. On the other hand, if the alignment is shifted in the z direction, the two alignment indicator images A1 and A2 are rendered at different positions. If the alignment is proper in all the xyz directions, as illustrated in FIG. 6B, the alignment indicator images A1 and A2 are rendered one on top of another inside the target image T.

The displacement of the alignment indicator images A1 and A2 with respect to the target image T (displacement amount, displacement direction) indicates the alignment shift in the xy directions (shift amount, shift direction). The displacement between the two alignment indicator images A1 and A2 (displacement amount, displacement direction) indicates the alignment shift in the z direction (shift amount, shift direction).

The analyzer 231 finds the shift of the alignment by analyzing the front image G1, and obtains the amount of movement of the optical system to cancel the shift. This process is performed, for example, in the following manner. First, the analyzer 231 specifies image regions corresponding to the alignment indicator images A1 and A2 based on pixel information (luminance values, etc.) of the front image G1. Then, the analyzer 231 specifies a characteristic position of each image region specified (the center, the center of gravity, etc.). Subsequently, the analyzer 231 finds the displacement of the characteristic position in each image region with respect to the center position of the target image T. Then, the analyzer 231 obtains a shift of the alignment based on the displacement to obtain the amount of movement of the optical system to cancel the shift of the alignment. Note that the analyzer 231 may store information that associates displacements of the alignment indicator images defined in the coordinate system of the front image with shifts of the alignment defined in the coordinate system of the real space in advance so that the shift of the alignment can be obtained with reference to this association information.

The image processor 230 that functions as described above includes, for example, the aforementioned microprocessor, RAM, ROM, a hard disk drive, a circuit board, and the like. The storage device such as a hard disk drive stores computer programs that cause the microprocessor to implement the above functions in advance.

(User Interface)

A user interface 240 includes the display 240A and an operation part 240B. The display 240A includes the aforementioned display device of the arithmetic and control unit 200 and the display device 3. The operation part 240B includes the aforementioned operation device of the arithmetic and control unit 200. The operation part 240B may include various types of buttons and keys provided on the case of the ophthalmologic apparatus 1 or the outside. For example, if the fundus camera unit 2 has a case similar to those of conventional fundus cameras, the operation part 240B may include a joy stick, an operation panel, and the like arranged on this case. Besides, the display 240A may include various types of display devices such as a touch panel and the like arranged on the case of the fundus camera unit 2.

Note that the display 240A and the operation part 240B need not be configured as separate devices. For example, a device like a touch panel having a display function integrated with an operation function can be used. In such cases, the operation part 240B includes this touch panel and a computer program. The content of operation via the operation part 240B is fed to the controller 210 as an electric signal. Moreover, operations and inputs of information may be performed by using a graphical user interface (GUI) displayed on the display 240A and the operation part 240B.

Operations

Figure 7:
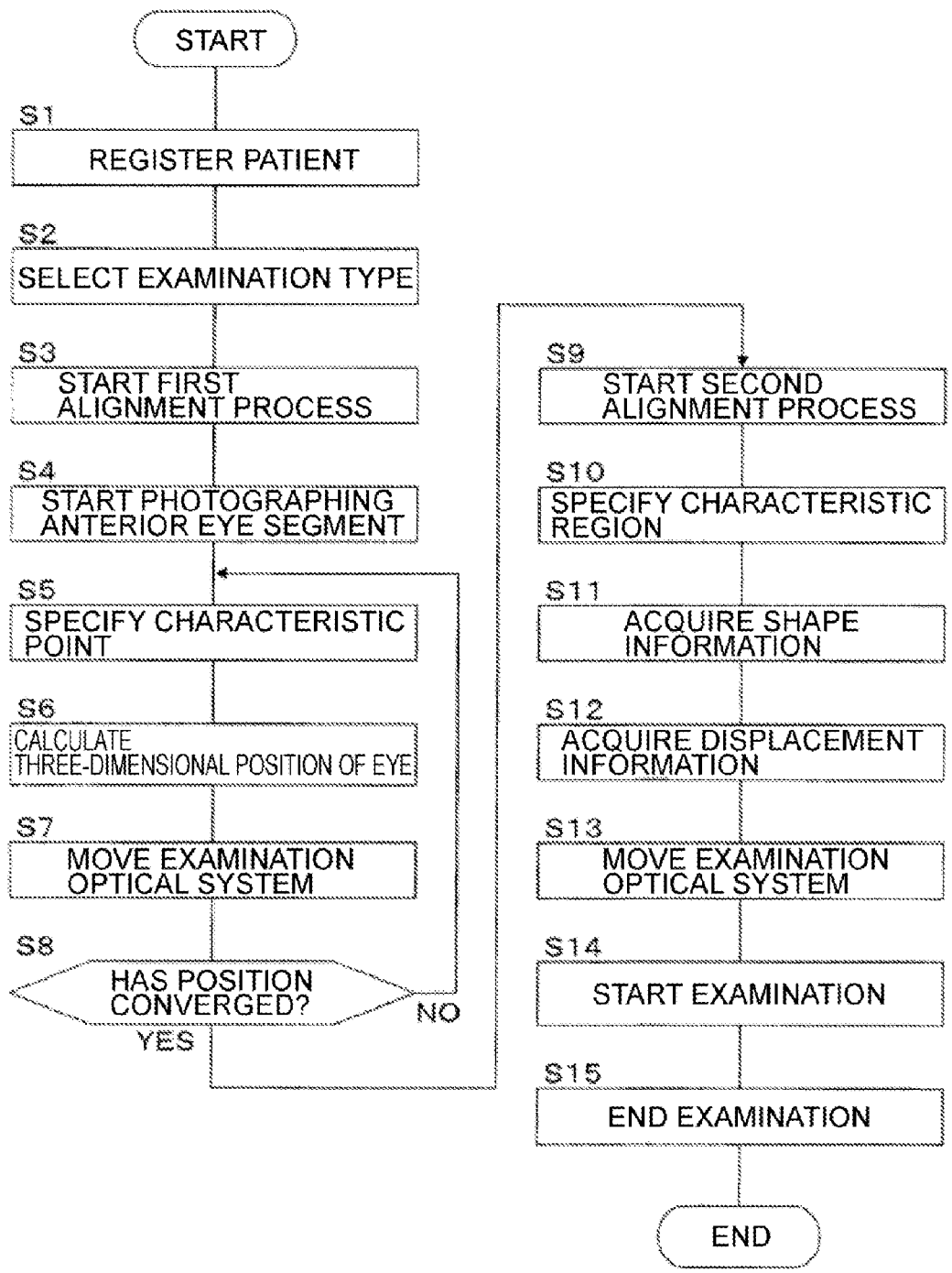
FIG. 7 is a flowchart illustrating an example of the operation of an ophthalmologic apparatus according to an embodiment.
Figure 8:
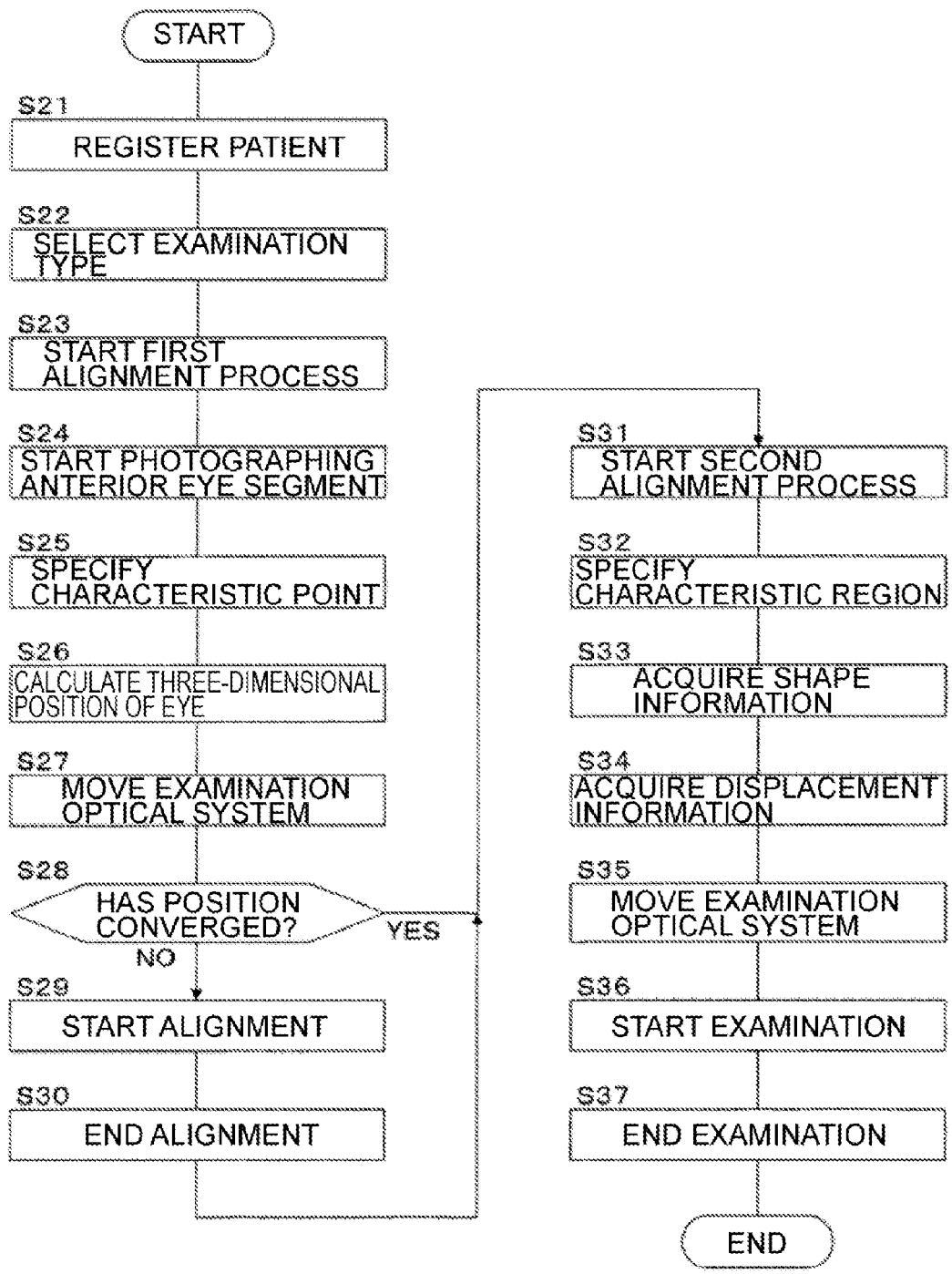
FIG. 8 is a flowchart illustrating an example of the operation of an ophthalmologic apparatus according to an embodiment.

Described below are operations of the ophthalmologic apparatus 1. FIGS. 7 and 8 illustrate examples of the operation of the ophthalmologic apparatus 1.

First Operation Example

The first operation example is described with reference to FIG. 7. In the first operation example, after a first alignment process of moving the examination optical system based on the three-dimensional position of the eye E, a second alignment process is performed for moving the examination optical system based on the displacement information of the eye E. In the first alignment process, the examination optical system is moved according to the spatial position of the eye E. In the second alignment process, the examination optical system is moved according to the state of eye movement of the eye E.

(S1: Register Patient)

First, the user inputs patient information on a subject using the user interface 240. The patient information may include a patient ID, patient name, and the like.

(S2: Select Examination Type)

Next, using the user interface 240, the user selects and inputs a type of examination to be performed for the subject. The items of the examination type may include, for example, examined sites (fundus center, fundus periphery, optic disc, macula, etc.), examined eyes (left eye, right eye, both eyes), image photographing patterns (only a fundus image, only an OCT image, or both), OCT scanning patterns (line scan, cross scan, radial scan, circle scan, three-dimensional scan, etc.)

It is assumed in this operation example that the periphery of the fundus Ef is selected as an examined site. Incidentally, for example, as in the case where the fundus center is selected as an examined site, if the second alignment process is not required or less required, it is possible to perform control for carrying out only the first alignment process.

(S3: Start First Alignment Process)

Once an examination type has been selected, an instruction is given to start the first alignment process. This start instruction may be automatically issued by the controller 210 in response to the selection of the examination type or may be manually issued by the user through the operation part 240B.

(S4: Start Photographing Anterior Eye Segment)

Having received the instruction to start the first alignment process, the controller 210 causes the anterior eye cameras 300A and 300B to start photographing the anterior eye segment Ea. This photographing is moving image photography of the anterior eye segment Ea as a photographed object. The anterior eye cameras 300A and 300B perform moving image photography at a predetermined frame rate. Here, the timings of photographing by the anterior eye cameras 300A and 300B may be synchronized by the controller 210. The anterior eye cameras 300A and 300B successively send acquired frames to the controller 210 in real time. The controller 210 associates the frames obtained by the anterior eye cameras 300A and 300B according to the photography timing. That is, the controller 210 associates the frames acquired substantially simultaneously by both the anterior eye cameras 300A and 300B with each other. This association is performed based on, for example, the abovementioned synchronous control or based on the input timings of the frames from the anterior eye cameras 300A and 300B. The controller 210 sends a pair of associated frames to the analyzer 231.

(S5: Specify Characteristic Point)

The image correction part 2311 corrects the distortion of each frame sent from the controller 210 based on the aberration information stored in the storage 212. This correction is performed in the abovementioned manner. The pair of frames with the distortion thereof corrected is sent to the characteristic point specifying part 2312.

The characteristic point specifying part 2312 analyzes each frame sent from the image correction part 2311, thereby carrying out a process for specifying a position in the frame corresponding to a characteristic point (the center of the pupil) of the anterior eye segment Ea.

In the case of failure to specify a characteristic point, after moving the anterior eye cameras 300A and 300B in a direction away from the supporter 440 and/or in a direction outward of the supporter 440, the process of specifying a characteristic point may be performed again. By moving the anterior eye cameras 300A and 300B in a direction away from the supporter 440, the distance increases between the anterior eye cameras 300A and 300B and the subject (the eye E). Accordingly, it is possible to photograph a wider area of the subject's face. Thus, the eye E is more likely to be placed in a suitable photographable area by means of the anterior eye cameras 300A and 300B. In addition, by moving the anterior eye cameras 300A and 300B outward of the supporter 440, the anterior eye cameras 300A and 300B are each moved in the directions of the respective ear side of the subject. Thus, the eye E is more likely to be placed in a suitable photographable area. Further, by combining the movements to these two directions, the eye E is far more likely to be placed in a suitable photographable area. Incidentally, if such a routine has been repeated predetermined times, it can be shifted to manual alignment.

Further, it is possible to determine whether an image corresponding to the anterior eye segment Ea is located within a predetermined area of the frame. Then, when the image of the anterior eye segment Ea is not located within the predetermined area of the frame, the anterior eye cameras 300A and 300B are controlled to move in the same manner as described above.

(S6: Calculate Three-Dimensional Position of Eye)

The three-dimensional position calculating part 2313 calculates the three-dimensional position of the characteristic point (the center of the pupil) of the eye E based on the positions of the anterior eye cameras 300A and 300B and the positions of the characteristic point specified by the characteristic point specifying part 2312 for the pair of frames. This process is performed in the abovementioned manner.

(S7: Move Examination Optical System)

Based on the three-dimensional position of the center of the pupil calculated in step S6, the controller 210 controls the optical system driver 2A to match the optical axis of the examination optical system with the axis of the eye E, and such that the distance from the eye E to the examination optical system becomes a specific working distance.

(S8: Has Position Converged?)

When the examination optical system has been moved in step S7, the controller 210 determines whether the position of the examination optical system has converged. This determination process is performed by, for example, using the alignment indicator. The observation condition of the alignment indicator changes depending on the alignment state. Specifically, when the alignment is in a suitable state, two images of the alignment indicator are observed in substantially the same position. On the other hand, as the alignment state becomes worse, the distance between the two images increases. The controller 210 calculates the distance between the two images captured by the CCD image sensor 35, and determines whether this distance is equal to or less than a predetermined threshold. When the distance is equal to or less than the threshold (YES in step S8), it is determined that the position of the examination optical system has converged, and the first alignment process ends. Thus, the process control moves to the second alignment process in step S9.

On the other hand, when the distance exceeds the threshold (NO in step S8), it is determined that the position of the examination optical system has not converged. Thus, the process control returns to step S5. Steps S5 to S8 are repeated until, for example, the determination result of "NO" is obtained predetermined times in step S8. When the determination result of "NO" is repeatedly obtained predetermined times in step S8, the controller 210 outputs, for example, predetermined warning information.

(S9: Start Second Alignment Process)

Having determined that the position of the examination optical system has converged (YES in step S8), the controller 210 ends the first alignment process, and starts the second alignment process.

(S10: Specify Characteristic Region)

The characteristic region specifying part 2314 analyzes each frame sent from the image correction part 2311 and thereby specifies a characteristic region (pupil region) in the frame corresponding to a characteristic site (pupil) of the anterior eye segment Ea.

(S11: Acquire Shape Information)

The shape information acquisition part 2315 analyzes the characteristic region specified in step S10, and thereby acquires shape information of the characteristic region (pupil region). This process is performed by, for example, calculating the major axis and the minor axis of an approximate ellipse of the pupil region.

(S12: Acquire Displacement Information)

The displacement information acquisition part 2316 acquires displacement information indicating the displacement direction and the displacement amount of the eye E due to eye movement based on the shape information acquired in step S11.

(S13: Move Examination Optical System)

With reference to the correspondence information 212*a*, the movement information specifying part 214 specifies a movement direction and movement amount corresponding to the displacement direction and the displacement amount indicated by the displacement information acquired in step S12. The controller 210 controls the optical system driver 2A to move the examination optical system in the movement direction by the movement amount. This movement of the examination optical system is made within the xy plane. With this, the second alignment process ends.

Incidentally, the controller 210 may control the optical system driver 2A to move the examination optical system in the z direction based on the movement amount in addition to the movement in the xy plane. This process of moving the examination optical system in the z direction corresponds to a third alignment process.

(S14: Start Examination)

Upon completion of the second alignment process in step S13, the controller 210 starts the examination selected in step S2.

(S15: End Examination)

Upon completion of the examination of the eye E, this operation ends.

Second Operation Example

The second operation example is described with reference to FIG. 8. In the second operation example, it is determined whether the first alignment process has succeeded or failed, and alignment is performed by using an alignment indicator if the process has failed. The second alignment process is performed after that.

(S21 to S27: Register Patient to Move Examination Optical System)

Steps S21 to S27 are performed in the same manner as steps S1 to S7 of the first operation example.

(S28: Position Converged?)

When the examination optical system has been moved in step S27, the controller 210 determines whether the position of the examination optical system has converged in the same manner as step S8. When it is determined that the position of the examination optical system has converged, that is, if the first alignment process has succeeded (YES in step S28), the process control moves to the second alignment process in step S31.

On the other hand, when it is determined that the first alignment process has failed (NO in step S28), the process control moves to alignment in step S29. Incidentally, the first alignment process is determined to have failed when the convergence determination process is repeated predetermined times.

(S29: Start Alignment)

Having determined that the first alignment process has failed (NO in step S28), the controller 210 performs the alignment mentioned above. This alignment may be automatic or manual alignment. In addition, automatic alignment may be performed first, and then manual alignment may be performed if the automatic alignment has failed.

(S30: End Alignment)

Upon completion of the alignment, the controller 210 starts the second alignment process in step S31.

(S31 to S37: Start Second Alignment Process to End Examination)

Steps S31 to S37 are performed in the same manner as steps S9 to S15 of the first operation example. Upon completion of the examination, this operation ends.

[Actions and Effects]

Described below are the actions and effects of the ophthalmologic apparatus 1.

The ophthalmologic apparatus 1 includes the examination optical system, the optical system driver 2A (drive part), the anterior eye cameras 300 (two or more imaging parts), the analyzer 231, and the controller 210. The examination optical system is an optical system for examining the eye E. The optical system driver 2A moves the examination optical system. The anterior eye cameras 300 substantially simultaneously photograph the anterior eye segment Ea of the eye E from different directions. The analyzer 231 analyzes photographic images captured by the anterior eye cameras 300 to obtain the three-dimensional position of the eye E. In addition, by analyzing the photographic images captured by the anterior eye cameras 300, the analyzer 231 acquires displacement information indicating the displacement direction and the displacement amount of the eye E due to eye movement. The controller 210 controls the optical system driver 2A based on the three-dimensional position of the eye E obtained by the analyzer 231 to move the examination optical system (the first alignment process). Further, the controller 210 controls the optical system driver 2A based on the displacement information obtained by the analyzer 231 to move the examination optical system (the second alignment process).

With the ophthalmologic apparatus 1, the examination optical system can be aligned according to the spatial location of the eye E by the first alignment process, and the examination optical system can be aligned according to the state of eye movement of the eye E by the second alignment process. Therefore, precise alignment can be achieved according to the state of the eye E, and thus the examination can be performed suitably. Note that the displacement direction includes at least one of, for example, horizontal direction, vertical direction, and cycloduction direction.

To obtain the displacement information used in the second alignment process, for example, the analyzer 231 includes the characteristic region specifying part 2314, the shape information acquisition part 2315, and the displacement information acquisition part 2316. The characteristic region specifying part 2314 analyzes each photographic image captured by the anterior eye cameras 300 to specify a characteristic region in the photographic image corresponding to the characteristic site of the anterior eye segment Ea. The shape information acquisition part 2315 analyzes the characteristic region specified to acquire shape information of the characteristic region. The displacement information acquisition part 2316 acquires displacement information indicating the displacement direction and the displacement amount of the eye E due to eye movement based on the shape information acquired.

The process for obtaining the displacement information is performed, for example, as follows. First, the characteristic region specifying part 2314 specifies the pupil region corresponding to the pupil or the iris region corresponding to the iris as the characteristic region. The shape information acquisition part 2315 obtains an approximate ellipse of the contour of the pupil region or the iris region specified, and calculates the major axis and the minor axis of the approximate ellipse, thereby obtaining the shape information. The displacement information acquisition part 2316 obtains the displacement direction based on the direction of the major axis or the minor axis indicated in the shape information, and obtains the displacement amount based on the ratio of the major axis and the minor axis (ellipticity). This approach is applicable to any characteristic site of the anterior eye segment Ea having a shape that can be approximated by an ellipse.

To obtain the three-dimensional position of the eye E to be used in the first alignment process, for example, the analyzer 231 includes the characteristic point specifying part 2312 and the three-dimensional position calculating part 2313. The characteristic point specifying part 2312 analyzes two photographic images captured substantially simultaneously by the anterior eye cameras 300A and 300B to specify positions in the photographic images corresponding to the characteristic point of the anterior eye segment Ea. The three-dimensional position calculating part 2313 calculates the three-dimensional position of the characteristic point in the real space based on the position corresponding to the characteristic point specified, and the positions of the anterior eye cameras 300A and 300B. The calculation result of the three-dimensional position of the characteristic point is used as the three-dimensional position of the eye E.

As described above, in this embodiment, a plurality of alignment processes are performed. For example, the alignment processes are performed in the order as follows. As a first example, the controller 210 may control to perform the second alignment process after the first alignment process. By performing in succession the first alignment process and the second alignment process in this manner, precise and quick alignment can be achieved.

As a second example, the controller 210 may perform alignment in response to the failure of the first alignment process, and then perform the second alignment process. In this case, the ophthalmologic apparatus 1 includes the alignment optical system 50 and a front image acquisition part. The alignment optical system 50 projects an alignment indicator on the anterior eye segment Ea. The front image acquisition part photographs the eye E on which the alignment indicator is being projected and thereby captures a front image of the anterior eye segment Ea. The illumination optical system 10 and the imaging optical system 30 correspond to the front image acquisition part. In addition, the analyzer 231 analyzes the front image thus acquired, and obtains the displacement of the examination optical system with respect to the eye E. The controller 210 determines whether the first alignment process has succeeded or failed. Having determined that the process has failed, the controller 210 performs the second alignment process after automatic alignment and/or manual alignment. According to this example, even when the first alignment process has failed, the second alignment process may be performed after performing spatial position matching of the examination optical system with respect to the eye E by the alignment. Incidentally, the success or failure of the first alignment process is affected by heights of noses and depths of eye depressions, and also by mascara, eyeshadow, and the like.

To move the examination optical system based on the displacement information, for example, the controller 210 includes the storage 212 (first storage) and the movement information specifying part 214 (first movement information specifying part). The storage 212 stores, in advance, the correspondence information 212a (first correspondence information) in which movement directions and movement amounts of the examination optical system are associated with displacement directions and displacement amounts of the eye E. Based on the correspondence information 212a, the movement information specifying part 214 specifies the movement direction and the movement amount corresponding to the displacement direction and the displacement amount indicated by the displacement information acquired by the analyzer 231. In the second alignment process, the controller 210 controls the optical system driver 2A to move the examination optical system in the movement direction by the movement amount specified by the movement information specifying part 214. Incidentally, the movement direction in the second alignment process is, for example, a direction perpendicular to the optical axis of the examination optical system (i.e., an arbitrary direction in the xy plane).

The controller 210 may move the examination optical system in the direction of the optical axis of the examination optical system (i.e., the z direction) based on the movement amount of the examination optical system in the second alignment process (third alignment process). The third alignment process is performed to compensate a shift in working distance resulting from the second alignment process.

Second Embodiment

In the first embodiment described above, the first alignment process in which the examination optical system is moved based on the three-dimensional position of the eye, and the second alignment process in which the examination optical system is moved based on the displacement of the eye due to eye movement. The second alignment process is performed by analyzing photographic images captured by two or more imaging parts. On the other hand, in the second embodiment, the second alignment process is performed based on the projection position of a fixation target. In the following, like reference numerals designate like parts as in the first embodiment.

[Configuration]

Figure 2:
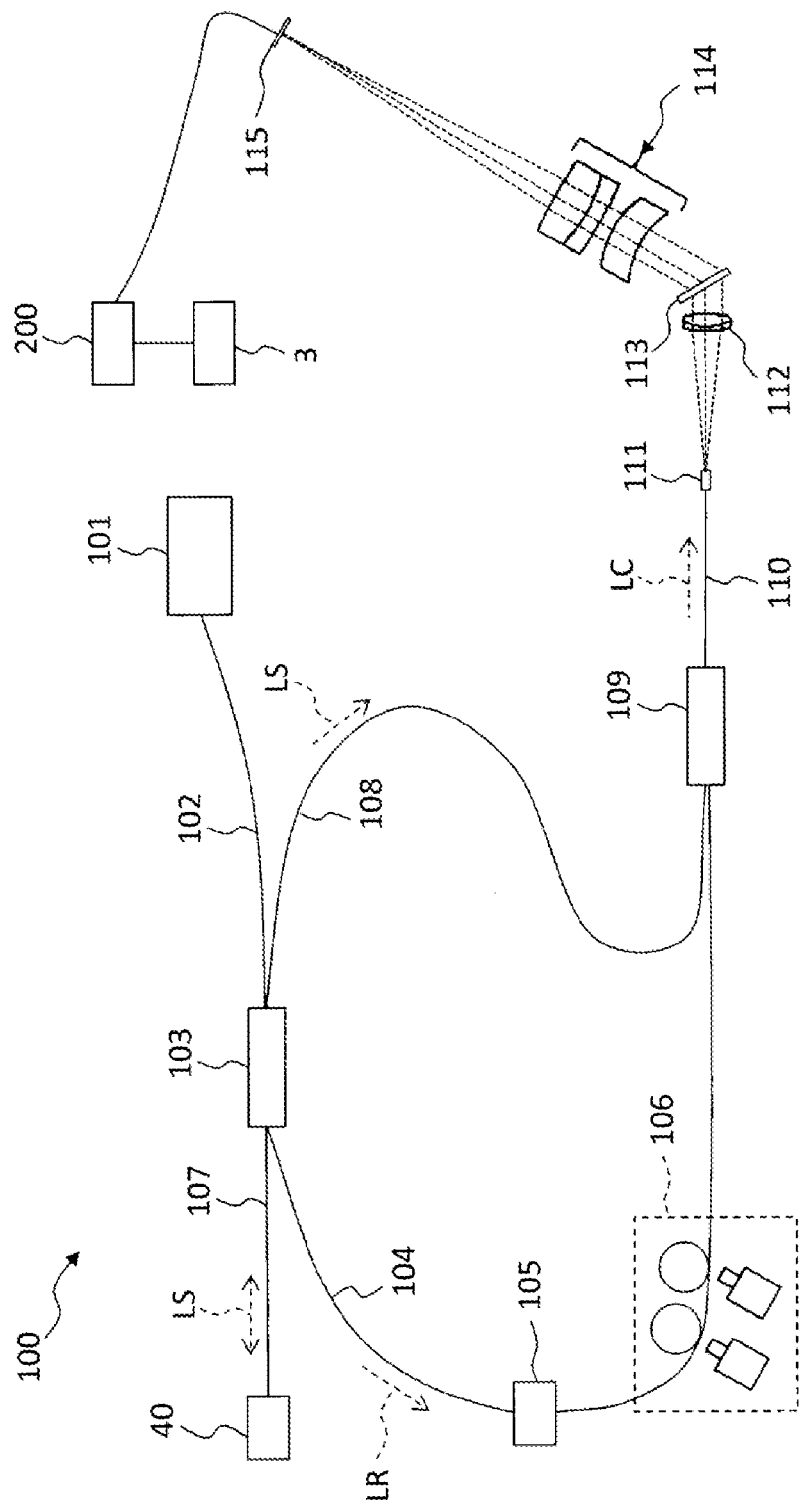
FIG. 2 is a schematic diagram illustrating an example of a configuration of an ophthalmologic apparatus according to an embodiment.
Figure 9:
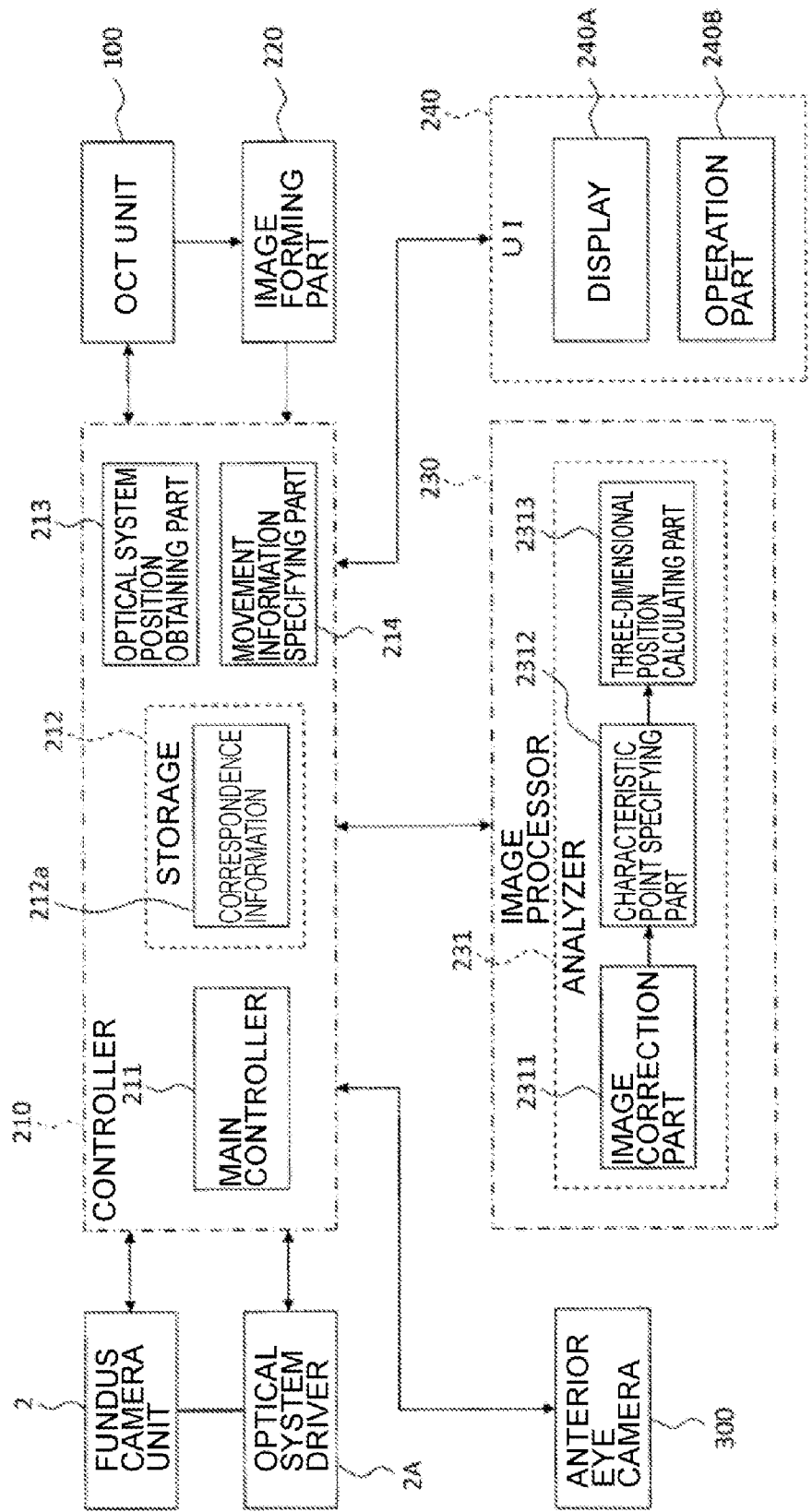
FIG. 9 is a schematic diagram illustrating an example of a configuration of an ophthalmologic apparatus according to an embodiment.

The ophthalmologic apparatus 1 of this embodiment has, for example, the same hardware configuration as that of the first embodiment (see FIGS. 1 and 2). FIG. 9 illustrates a configuration example of the control system of the ophthalmologic apparatus 1 of this embodiment. The control system is mainly different from that of the first embodiment illustrated in FIG. 3 in the absence of the characteristic region specifying part 2314, the shape information acquisition part 2315, and the displacement information acquisition part 2316. That is, the analyzer 231 of this embodiment does not acquire the displacement information to be used in the second alignment process. In the following, differences from the first embodiment are mainly described.

As described above, in this embodiment, the second alignment process is performed based on the projection position of the fixation target. The projection of the fixation target is performed by a fixation optical system. The fixation optical system includes a fixation target presenting part (the LCD 39) for presenting a fixation target and a fixation target projection optical system for projecting the fixation target onto the eye E. In the example of FIG. 1, the fixation target projection optical system is constituted by optical elements that form the optical path between the LCD 39 and the eye E. Specifically, the fixation target projection optical system of this example includes the half mirror 39A, the mirror 32, the focusing lens 31, the objective lens 22, and the like.

The controller 210 displays the fixation target, for example, in a position of the LCD 39 corresponding to an examined site designated by the user. The examined site is associated with the display position of the fixation target in advance. The display position of the fixation target may be arbitrarily changed by using the operation part 240B.

The storage 212 stores, in advance, the correspondence information 212a as the second correspondence information. In the correspondence information 212a of this embodiment, unlike the first embodiment, movement directions and movement amounts of the examination optical system are associated with projection positions of the fixation target. Here, the projection positions of the fixation target correspond to fixation positions (fixation directions) and examination positions of an eye. As in the first embodiment, the correspondence information 212a is created based on the results of simulation and actual measurement. The correspondence information 212a is created only for the case where eye movement works well, for example, as in the case of examining the fundus periphery. Besides, in the correspondence information 212a, a movement direction and a movement amount may be associated with each of a plurality of display positions of the fixation target on the LCD 39, The display positions may be all positions capable of displaying the fixation target on the LCD 39, or may be part of them (e.g., only in the case where the fixation position is separated more than a predetermined distance from the center of the fundus).

When a position of the fixation target projected by the fixation optical system is set, the movement information specifying part 214 of this embodiment specifies the movement direction and the amount of movement of the examination optical system corresponding to the projection position based on the correspondence information 212a.

[Operation]

Figure 10:
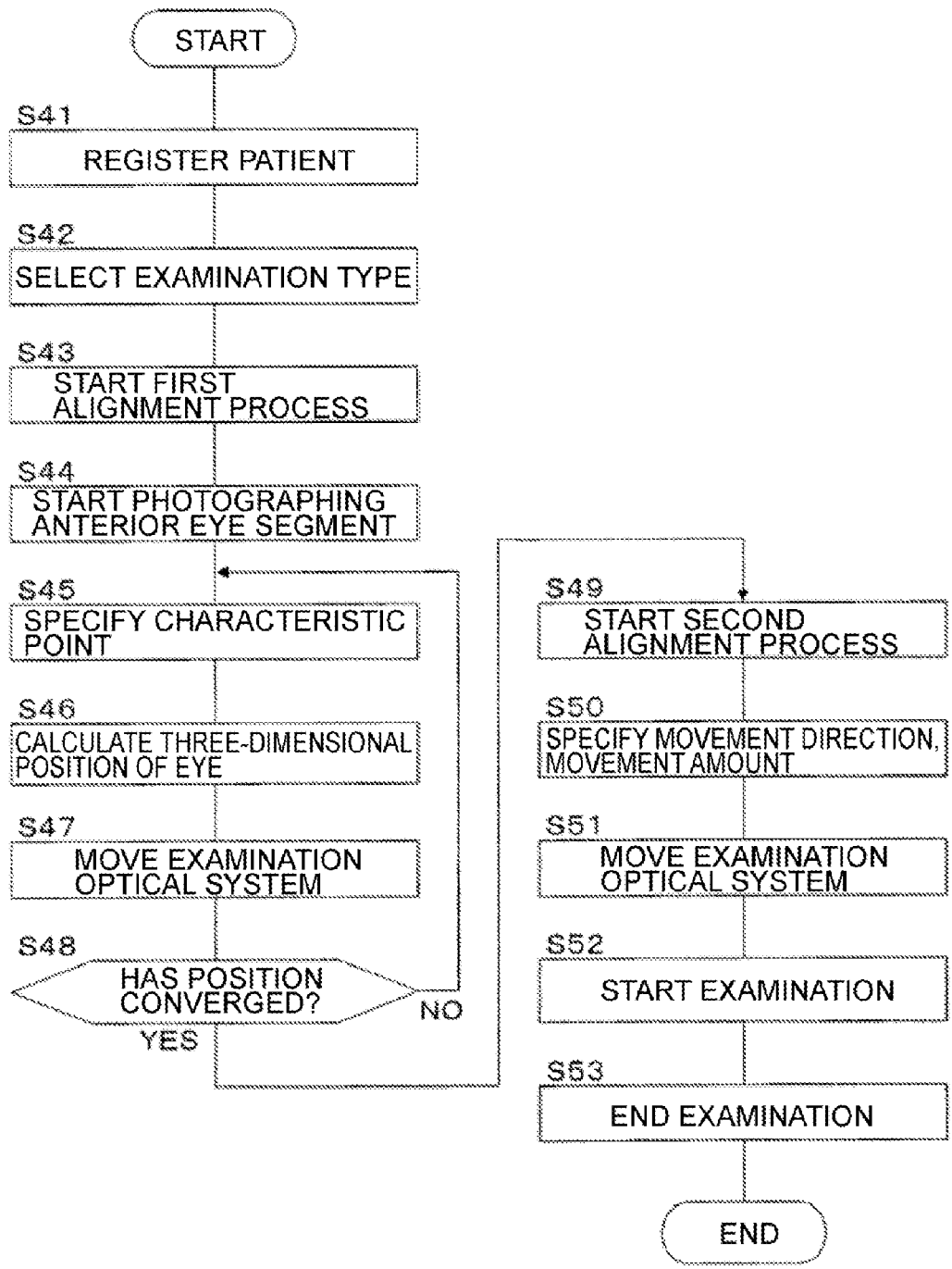
FIG. 10 is a flowchart illustrating an example of the operation of an ophthalmologic apparatus according to an embodiment.
Figure 11:
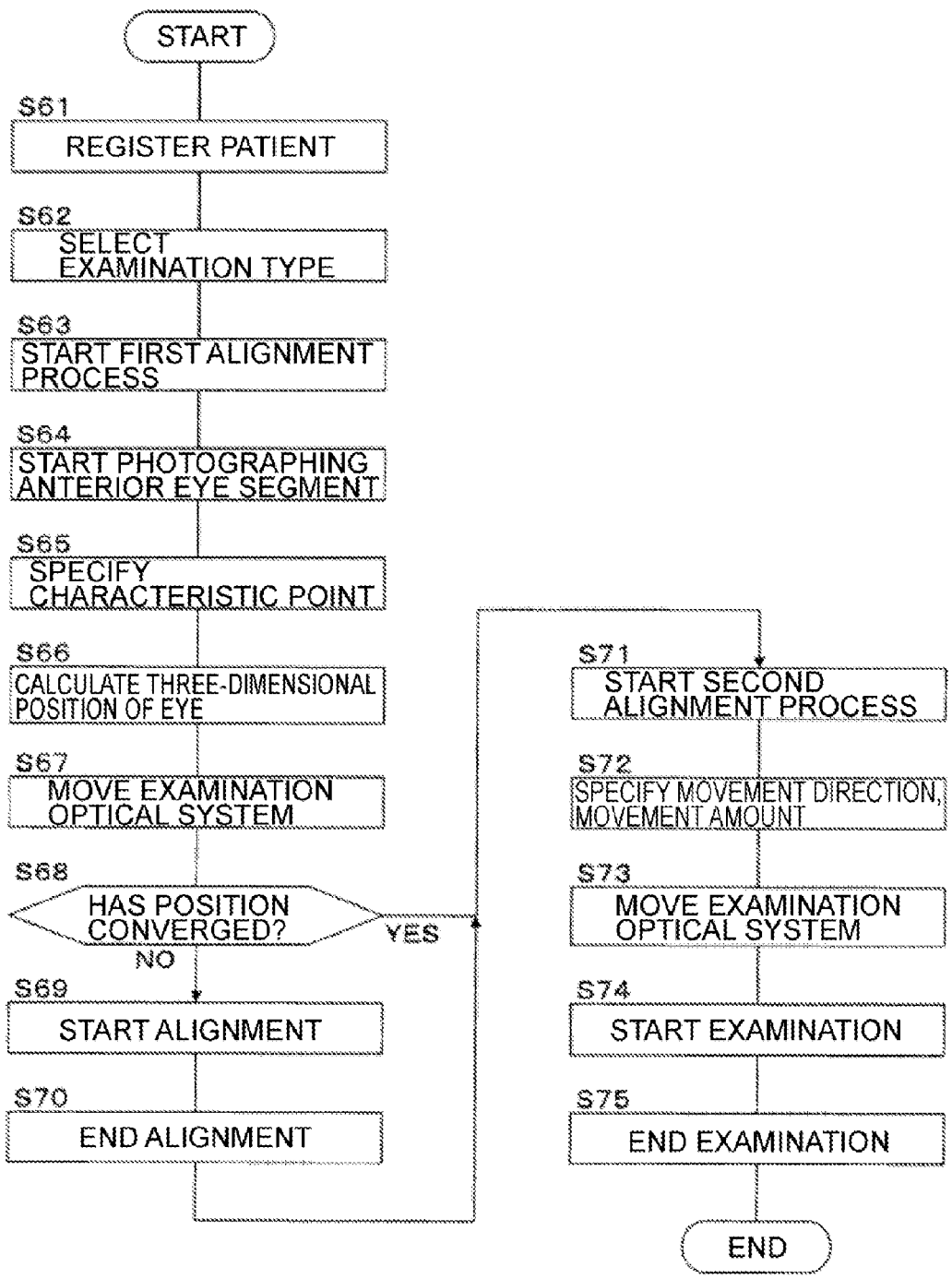
FIG. 11 is a flowchart illustrating an example of the operation of an ophthalmologic apparatus according to an embodiment.

Described below are operations of the ophthalmologic apparatus 1 of this embodiment. FIGS. 10 and 11 illustrate an example of the operation of the ophthalmologic apparatus 1.

First Operation Example

The first operation example is described with reference to FIG. 10. In the first operation example, after the first alignment process of moving the examination optical system based on the three-dimensional position of the eye E, the second alignment process is performed for moving the examination optical system based on the projection position of a fixation target. In the first alignment process, the examination optical system is moved according to the spatial position of the eye E. In the second alignment process, the examination optical system is moved according to the fixation position inducing eye movement of the eye E.

(S41 to S49: Register Patient to Start Second Alignment Process)

Steps 41 to 49 are performed in the same manner as steps 1 to 9 of the first operation example. That is, the first alignment process, the transition from the first alignment process to the second alignment process, etc. are similarly performed to those of the first embodiment. Note that, in this embodiment, an examination position (i.e., fixation position) is selected for the selection of an examination type in step S42. The controller 210 controls the LCD 39 to display the fixation target in a display position corresponding to the selected fixation position.

(S50: Specify Movement Direction, Movement Amount)

In the second alignment process, the movement information specifying part 214 specifies the movement direction and the movement amount corresponding to the position of the fixation target projected by the fixation optical system selected in step S42 with reference to the correspondence information 212a.

(S51: Move Examination Optical System)

The controller 210 controls the optical system driver 2A based on the movement direction and the movement amount specified in step S50 to move the examination optical system.

(S52, S53: Start Examination, End Examination)

Steps S52 and S53 are performed in the same manner as steps S14 and S15 in the first operation example. Upon completion of the examination, this operation ends.

Second Operation Example

The second operation example is described with reference to FIG. 11. In the second operation example, it is determined whether the first alignment process has succeeded or failed, and alignment is performed by using an alignment indicator if the process has failed. The second alignment process is performed after that.

(S61 to S67: Register Patient to Move Examination Optical System)

Steps S61 to S67 are performed in the same manner as steps S41 to S47 of the first operation example.

(S68: Has Position Converged?)

When the examination optical system has been moved in step S67, the controller 210 makes a determination on the convergence in the same manner as step S8 in the first alignment process. When it is determined that the position of the examination optical system has converged, that is, if the first alignment process has succeeded (YES in step S68), the process control moves to the second alignment process in step S71.

On the other hand, when it is determined that the first alignment process has failed (NO in step S68), the process control moves to alignment in step S69. Incidentally, the first alignment process is determined to have failed when the convergence determination process is repeated predetermined times.

(S69, S70: Start Alignment, End Alignment)

Having determined that the first alignment process has failed in step S68, the controller 210 performs the same alignment as in the first embodiment. Upon completion of the alignment, the controller 210 moves to the second alignment process in step S71.

(S71 to S75: Start Second Alignment Process to End Examination)

Steps 71 to 75 are performed in the same manner as steps 49 to 53 of the first operation example. Upon completion of the examination, this operation ends.

[Actions and Effects]

Described below are the actions and effects of the ophthalmologic apparatus 1 of the second embodiment.

The ophthalmologic apparatus 1 includes the examination optical system, the optical system driver 2A (drive part), the fixation optical system, the anterior eye cameras 300 (two or more imaging parts), the analyzer 231, and the controller 210. The examination optical system is an optical system for examining the eye E. The optical system driver 2A moves the examination optical system. The fixation optical system projects a fixation target for visual guidance onto the subject's eye. The anterior eye cameras 300 substantially simultaneously photograph the anterior eye segment Ea of the eye E from different directions. The analyzer 231 analyzes photographic images captured by the anterior eye cameras 300 to obtain the three-dimensional position of the eye E. The controller 210 controls the fixation optical system to change the projection position of the fixation target. The controller 210 controls the optical system driver 2A based on the three-dimensional position of the eye E obtained by the analyzer 231 to move the examination optical system (the first alignment process). Further, the controller 210 controls the optical system driver 2A based on the projection position of the fixation target to move the examination optical system (the second alignment process).

With the ophthalmologic apparatus 1, the examination optical system can be aligned according to the spatial location of the eye E by the first alignment process, and the examination optical system can be aligned according to the fixation position for bringing the eye movement of the eye E to a predetermined state by the second alignment process. Therefore, precise alignment can be achieved according to the state of the eye E, and thus the examination can be performed suitably.

To perform the second alignment process, for example, the controller 210 includes the storage 212 (second storage) and the movement information specifying part 214 (second movement information specifying part). The storage 212 stores, in advance, the correspondence information 212a in which movement directions and movement amounts of the examination optical system are associated with projection positions of the fixation target. The movement information specifying part 214 specifies the movement direction and the movement amount corresponding to the position of the fixation target projected by the fixation optical system based on the correspondence information 212a. The controller 210 performs the second alignment process based on the movement direction and the movement amount specified.

To change the fixation position, for example, the fixation optical system includes the LCD 39 (fixation target presenting part) and a fixation target projection optical system. The LCD 39 is capable of presenting a fixation target at a plurality of positions. The fixation target projection optical system projects the fixation target onto the eye E. In this configuration example, in the correspondence information 212a, a movement direction and a movement amount of the examination optical system are associated with each of the plurality of positions. The controller 210 controls the LCD 39 to present the fixation target in one of the abovementioned positions. The movement information specifying part 214 specifies the movement direction and the movement amount corresponding to the position where the fixation target is presented by the controller 210 based on the correspondence information 212a.

As described above, a plurality of alignment processes are performed in this embodiment. For example, the alignment processes are performed in the order as follows. As a first example, the controller 210 may control to perform the second alignment process after the first alignment process. By performing in succession the first alignment process and the second alignment process in this manner, precise and quick alignment can be achieved.

As a second example, the controller 210 may perform alignment in response to the failure of the first alignment process, and then perform the second alignment process. In this case, the ophthalmologic apparatus 1 includes the alignment optical system 50 and a front image acquisition part. The alignment optical system 50 projects an alignment indicator on the anterior eye segment Ea. The front image acquisition part photographs the eye E on which the alignment indicator is being projected and thereby acquires a front image of the anterior eye segment Ea. The illumination optical system 10 and the imaging optical system 30 correspond to the front image acquisition part. In addition, the analyzer 231 analyzes the front image thus acquired, and obtains the displacement of the examination optical system with respect to the eye E. The controller 210 determines whether the first alignment process has succeeded or failed. Having determined that the process has failed, the controller 210 performs the second alignment process after automatic alignment and/or manual alignment. According to this example, even when the first alignment process has failed, the second alignment process may be performed after the examination optical system has been spatially aligned with the eye E by the alignment.

In this embodiment, the movement direction of the examination optical system in the second alignment process can be a direction perpendicular to the optical axis of the examination optical system (i.e., xy directions). Further, the controller 210 may move the examination optical system in the direction of the optical axis of the examination optical system (i.e., the z direction) based on the movement amount of the examination optical system in the second alignment process (third alignment process). The third alignment process is performed to compensate a shift in working distance resulting from the second alignment process.

To obtain the three-dimensional position of the eye E to be used in the first alignment process, for example, the characteristic point specifying part 2312 and the three-dimensional position calculating part 2313 may be provided as in the first embodiment.

Third Embodiment

The third embodiment describes various controls according to the miosis state of the subject's eye. In the following, like reference numerals designate like parts as in the first embodiment.

[Configuration]

Figure 12:
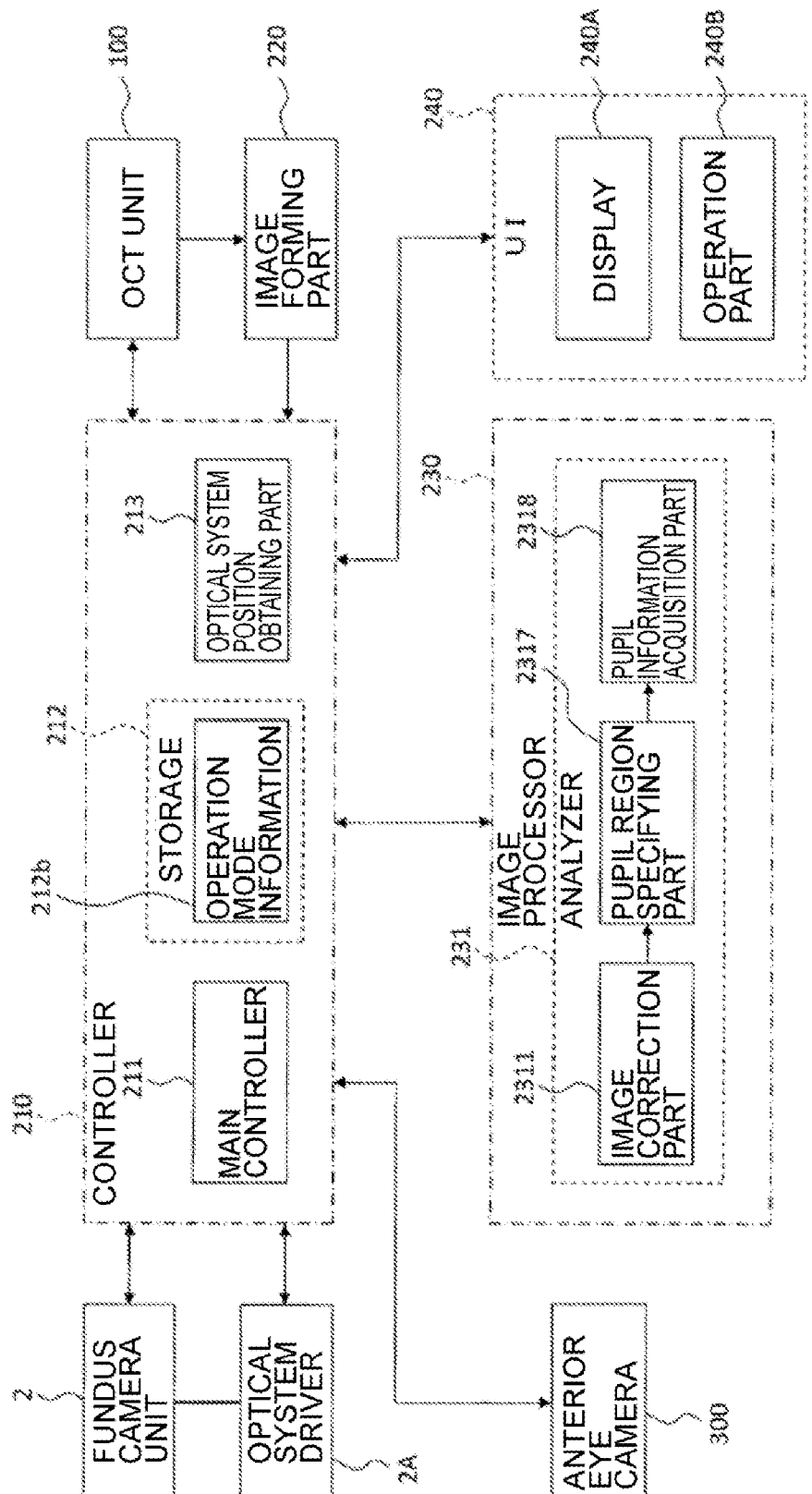
FIG. 12 is a schematic diagram illustrating an example of a configuration of an ophthalmologic apparatus according to an embodiment.

The ophthalmologic apparatus 1 of this embodiment has, for example, the same hardware configuration as that of the first embodiment (see FIGS. 1 and 2). FIG. 12 illustrates a configuration example of the control system of the ophthalmologic apparatus 1 of this embodiment. In this example, a description is given of a configuration capable of switching operation modes between one for a normal pupil eye having a general pupil diameter and one for small pupil eye.

The storage 212 stores operation mode information 212b in advance. In the operation mode information 212b, various control contents are associated with pupil information indicating states of a pupil. The pupil information may include pupil sizes (pupil diameters, etc.) and/or pupil shapes. The control contents may include fixation light intensities, observation light intensities, imaging light intensities, diaphragms, positions of the examination optical system, and the like.

The fixation light intensity indicates the intensity of a light flux projecting the fixation target onto the eye E. The fixation light intensity is controlled by, for example, controlling the light emission intensity of the LCD 39. The observation light intensity indicates the intensity of illumination light for observation. The observation light intensity is controlled by, for example, controlling the light emission intensity of the observation light source 11. The imaging light intensity indicates the intensity of illumination light for photographing. The imaging light intensity is controlled by controlling the output intensity of the imaging light source 15. The diaphragm is controlled by, for example, switching the aperture between one for normal pupil eye and one for small pupil eye. The diaphragm control includes control of selectively applying two diaphragms (apertures) having different aperture sizes and control of changing aperture size. The diaphragm to be controlled is, for example, the diaphragm 19 of the illumination optical system 10 illustrated in FIG. 1. The position of the examination optical system is controlled, for example, such that the position is shifted for the small pupil eye. Incidentally, the shift amount may vary according to the pupil size.

Figure 13:
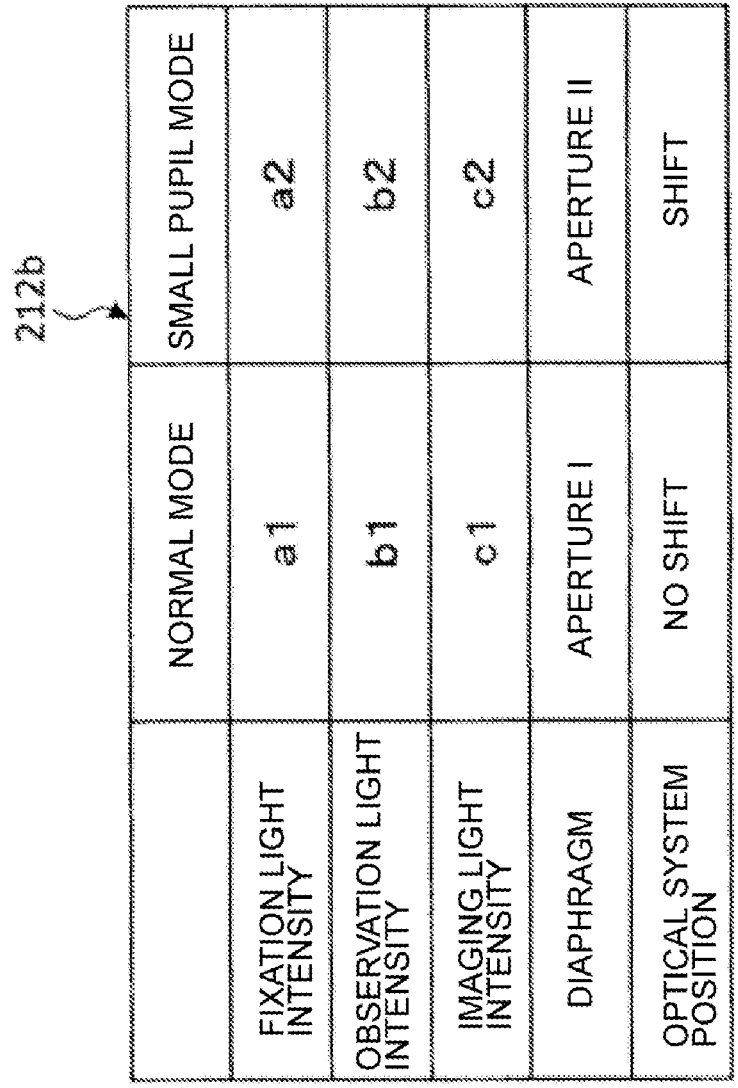
FIG. 13 is a schematic diagram illustrating an example of a configuration of an ophthalmologic apparatus according to an embodiment.

FIG. 13 illustrates an example of the operation mode information 212b. In the operation mode information 212b, as control contents corresponding to the normal mode to be applied to the normal pupil eye, fixation light intensity "a1", observation light intensity "b1", imaging light intensity "c1", aperture "I", and optical system position "no shift" are associated with one another. Similarly, as control contents corresponding to the small pupil mode to be applied to the small pupil eye, fixation light intensity "a2", observation light intensity "b2", imaging light intensity "c2", aperture "II", and optical system position "shift" are associated with one another. Incidentally, the fixation light intensity, the observation light intensity, and the imaging light intensity are defined by values of the light intensity or amounts equivalent thereto (voltage values, current values, charge amounts, etc.). In addition, the apertures "I" and "II" indicate identification information attached to the two apertures. As the optical system position, a shift amount may be used in place of "shift".

The analyzer 231 includes the image correction part 2311, a pupil region specifying part 2317, and a pupil information acquisition part 2318. The image correction part 2311 performs the same processing as in the first embodiment. The pupil region specifying part 2317 performs the same processing as the process of specifying a pupil region as described in the first embodiment (the characteristic point specifying part 2312). The pupil information acquisition part 2318 analyzes the pupil region specified by the pupil region specifying part 2317 and thereby acquires the pupil size and the pupil shape. The pupil size is acquired, for example, in the same manner as in the process of obtaining the major axis of an ellipse approximating the contour of the pupil region performed by the shape information acquisition part 2315 in the second embodiment. The pupil shape is also acquired, for example, in the same manner as the process of obtaining the ellipticity of an ellipse approximating the contour of the pupil region performed by the shape information acquisition part 2315. Although not illustrated, as in the first embodiment, the analyzer 231 analyzes photographic images captured by the anterior eye cameras 300 and obtains the three-dimensional position of the eye E.

The controller 210 performs an alignment process of moving the examination optical system by controlling the optical system driver 2A based on the three-dimensional position of the eye E obtained by the analyzer 231. Further, the controller 210 performs an optical system control process of controlling the optical system based on pupil information obtained by the analyzer 231. Examples of items to be controlled for the optical system include, as described above, fixation light intensity, observation light intensity, imaging light intensity, diaphragm, the position of the examination optical system, and the like.

[Operation]

Figure 14:
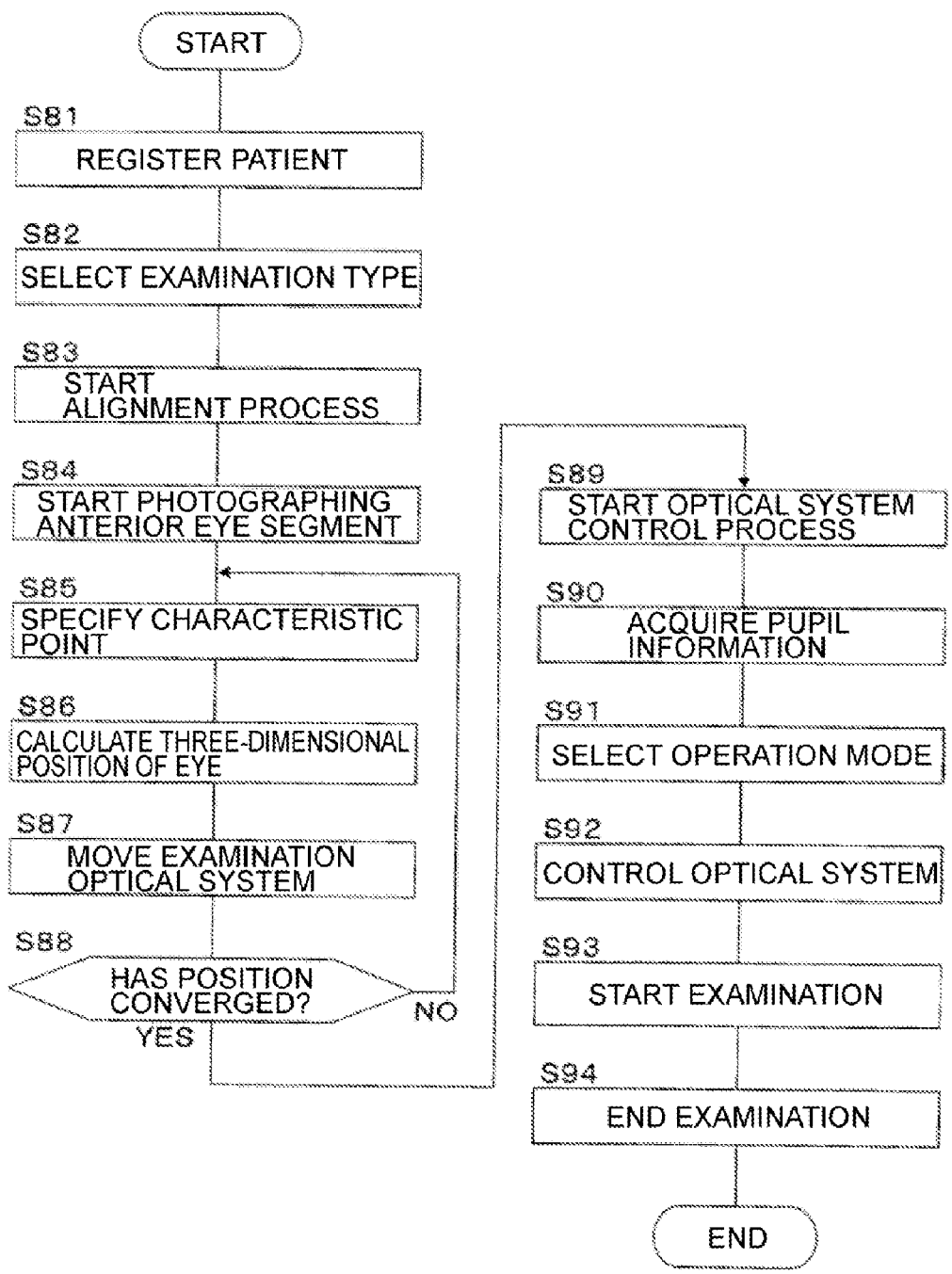
FIG. 14 is a flowchart illustrating an example of the operation of an ophthalmologic apparatus according to an embodiment.

Described below is an operation of the ophthalmologic apparatus 1. FIG. 14 illustrates an example of the operation of the ophthalmologic apparatus 1.

(S81 to S89: Register Patient to Start Optical System Control Process)

Steps S81 to S88 are performed in the same manner as steps S1 to S8 of the first operation example. That is, the alignment process (the first alignment process in the first embodiment) and the transition to the subsequent process are similar to those of the first embodiment.

(S90: Acquire Pupil Information)

In response to the transition from the alignment process to the optical system control process, the analyzer 231 acquires pupil information of the eye E by the above process, for example. The pupil information includes the pupil size and the pupil shape.

(S91: Select Operation Mode)

The controller 210 selects the normal mode or the small pupil mode based on the pupil information acquired in step S90. In this process, for example, the pupil size obtained in step S90 is compared with a preset threshold. If the pupil size exceeds the threshold, the controller 210 selects the normal mode. On the other hand, if the pupil size is equal to or less than the threshold, the controller 210 selects the small pupil mode.

(S92: Control Optical System)

The controller 210 acquires control contents corresponding to the operation mode selected in step S91 from the operation mode information 212b. The controller 210 performs control based on the control content for each of the fixation light intensity, the observation light intensity, the imaging light intensity, the diaphragm, and the position of the examination optical system.

(S93, S94: Start Examination, End Examination)

Steps S93 and S94 are performed in the same manner as steps S14 and S15 in the first operation example. Upon completion of the examination, this operation ends.

[Actions and Effects]

Described below are the actions and effects of the ophthalmologic apparatus 1.

The ophthalmologic apparatus 1 includes an optical system, the optical system driver 2A (the drive part), the anterior eye cameras 300 (two or more imaging parts), the analyzer 231, and the controller 210. The optical system includes an examination optical system for examining the eye E. The optical system driver 2A moves the examination optical system. The anterior eye cameras 300 substantially simultaneously photograph the anterior eye segment Ea of the eye E from different directions. The analyzer 231 analyzes photographic images captured by the anterior eye cameras 300 to obtain the three-dimensional position of the eye E. In addition, by analyzing the photographic images captured by the anterior eye cameras 300, the analyzer 231 acquires pupil information indicating the state of the pupil of the eye E. The controller 210 controls the optical system driver 2A based on the three-dimensional position of the eye E obtained by the analyzer 231 to move the examination optical system (the alignment process). Further, the controller 210 controls the optical system based on the pupil information acquired by the analyzer 231 (the optical system control process).

With the ophthalmologic apparatus 1, the examination optical system can be aligned according to the spatial location of the eye E by the alignment process, and the optical system is controlled by the optical system control process according to the state of the pupil of the eye E. Therefore, precise alignment and control can be achieved according to the state of the eye E, and thus the examination can be performed suitably. In addition, the operation mode can be changed automatically according to the state of the pupil. Moreover, by analyzing a plurality of photographic images captured from different directions by the anterior eye cameras 300, the state of the pupil of the eye E can be obtained with high accuracy and precision.

The optical system control process includes the control of at least one of, for example, the fixation light intensity, the observation light intensity, the imaging light intensity, the diaphragm, and the position of the optical system.

Described below is a configuration example for controlling the fixation light intensity. The optical system includes a fixation optical system that projects a fixation target for visual guidance onto the subject's eye. The analyzer 231 acquires the pupil size as the pupil information. The controller 210 controls the fixation optical system based on the pupil size to change the intensity of the light flux projecting the fixation target.

Described below is a configuration example for controlling the observation light intensity. The optical system includes the illumination optical system 10 (first illumination optical system) that is arranged coaxially with the examination optical system and irradiates the eye E with observation illumination light (continuous light), and the imaging optical system 30 (first imaging optical system) that is arranged coaxially with the examination optical system and captures a moving image of the eye E on which the observation illumination light is being irradiated. In the case in which the observation of the eye E corresponds to "examination", the illumination optical system 10 and the imaging optical system 30 are included in the examination optical system. The analyzer 231 acquires the pupil size as the pupil information. The controller 210 controls the illumination optical system 10 based on the pupil size to change the intensity (amount) of the observation illumination light.

Described below is a configuration example for controlling the imaging light intensity. The optical system includes the illumination optical system 10 (second illumination optical system) that is arranged coaxially with the examination optical system and irradiates the eye E with imaging illumination light (flash light), and the imaging optical system 30 (second imaging optical system) that is arranged coaxially with the examination optical system and captures an image of the eye E in synchronization with the irradiation of the imaging illumination light. In the case in which the observation of the eye E corresponds to "examination", the illumination optical system 10 and the imaging optical system 30 are included in the examination optical system. The analyzer 231 acquires the pupil size as the pupil information. The controller 210 controls the illumination optical system 10 based on the pupil size to change the intensity (amount) of the imaging illumination light.

Described below is a configuration example for controlling the diaphragm. The optical system includes the illumination optical system 10 (third illumination optical system) that is arranged coaxially with the examination optical system, includes two or more diaphragms (the diaphragm 19) with different aperture sizes, and irradiates the eye E with illumination light, and the imaging optical system 30 (third imaging optical system) that is arranged coaxially with the examination optical system and captures an image of the eye E irradiated by the illumination light. In the case in which the observation of the eye E corresponds to "examination", the illumination optical system 10 and the imaging optical system 30 are included in the examination optical system. The analyzer 231 acquires the pupil size as the pupil information. The controller 210 selectively places the two or more diaphragms in the optical path of the illumination optical system 10 based on the pupil size acquired.

Described below is a configuration example for controlling the position of the optical system. The analyzer 231 acquires the pupil shape as the pupil information. The controller 210 controls the drive part based on the acquired pupil shape to move the examination optical system. This movement control can include the process of another embodiment.

Fourth Embodiment

The fourth embodiment describes a process according to the state of blink of an eye. In the following, like reference numerals designate like parts as in the first embodiment.

Figure 15:
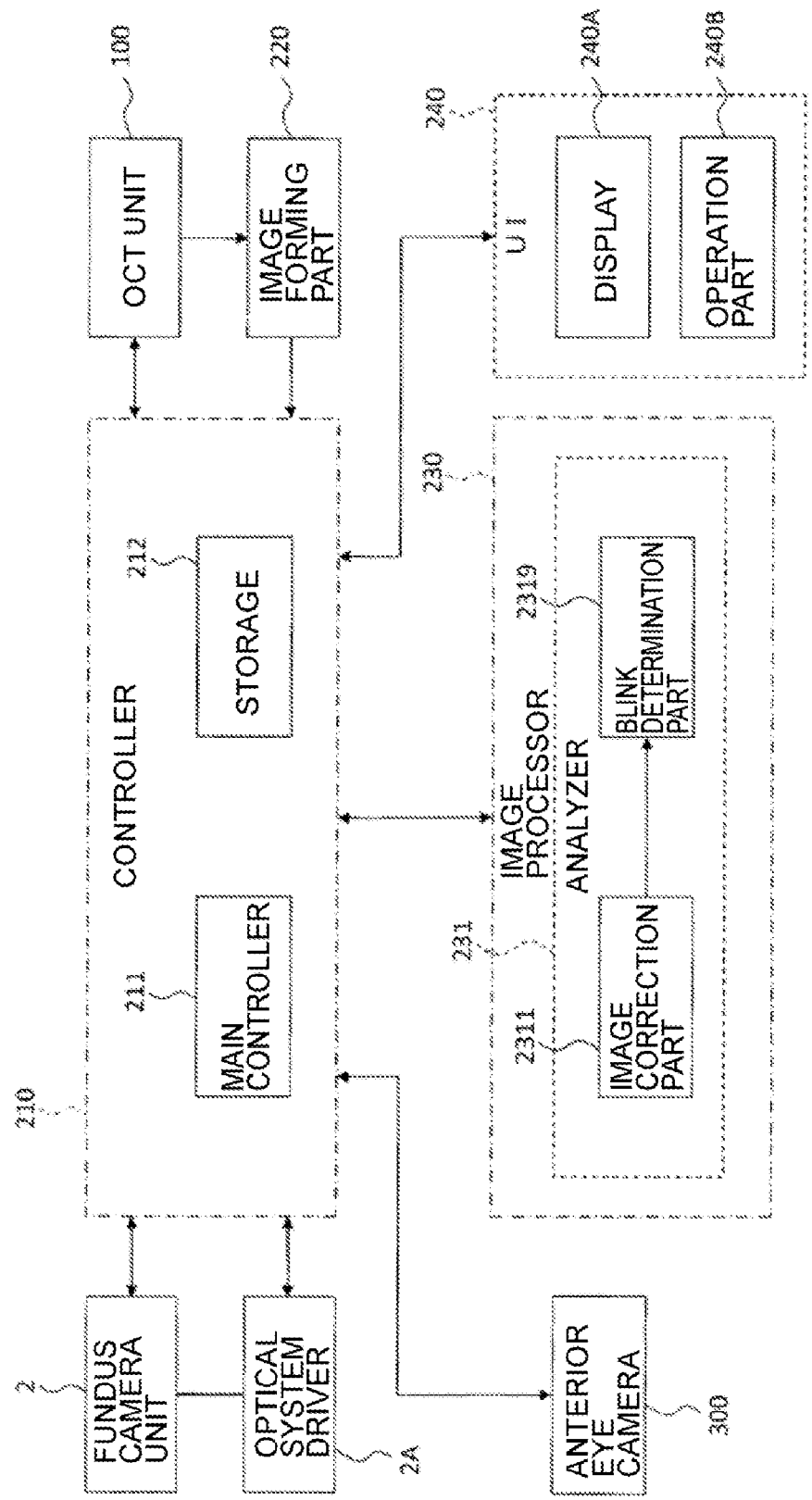
FIG. 15 is a schematic diagram illustrating an example of a configuration of an ophthalmologic apparatus according to an embodiment.

The ophthalmologic apparatus 1 of this embodiment has, for example, the same hardware configuration as that of the first embodiment (see FIGS. 1 and 2). FIG. 15 illustrates a configuration example of the control system of the ophthalmologic apparatus 1 of this embodiment.

The analyzer 231 includes the image correction part 2311 and a blink determination part 2319. The image correction part 2311 performs for example, the same processing as in the first embodiment. The blink determination part 2319 analyzes photographic images captured by the anterior eye cameras 300 and thereby determines whether the eye E is blinking. This process is performed, for example, in the following manner. First, the blink determination part 2319 specifies a pupil region (or an iris region) by analyzing photographic images. This process is performed, for example, in the same manner as in the first embodiment. If the pupil region is not specified, the blink determination part 2319 determines that the eye E is blinking. If a pupil region is specified, the blink determination part 2319 obtains shape information indicating the shape of the pupil region. The blink determination part 2319 makes a determination on the presence or absence of a blink based on the shape information. This process is performed based on, for example, the diameter of the pupil region in the vertical direction (y direction). When the diameter in the vertical direction is equal to or less than a predetermined threshold, the blink determination part 2319 determines that the eye E is blinking. On the other hand, when the diameter in the vertical direction exceeds the predetermined threshold, the blink determination part 2319 determines that the eye E is not blinking. For another example, the blink determination part 2319 obtains the ratio of the diameter of the pupil region in the vertical direction (y direction) to the diameter in the horizontal direction (x direction). When the ratio is equal to or less than a predetermined threshold, the blink determination part 2319 determines that the eye E is blinking. On the other hand, when the ratio exceeds the predetermined threshold, the blink determination part 2319 determines that the eye E is not blinking. Although not illustrated, as in the first embodiment, the analyzer 231 analyzes photographic images captured by the anterior eye cameras 300 and obtains the three-dimensional position of the eye E.

The ophthalmologic apparatus 1 provides a notification on the result of determination by the blink determination part 2319. As a specific example of the notification process, when it is determined by the blink determination part 2319 that the eye E is blinking, the controller 210 displays predetermined warning information on the display 240A. This warning information is character string information or image information indicating that the eye is blinking or calling attention. The mode of the display information may be switched between when the eye is blinking and when not blinking. The mode of the display information may be changed according to the time of blinking. For example, the mode of the display information may be changed if the duration of blinking exceeds a predetermined threshold.

Described below are the actions and effects of the ophthalmologic apparatus 1 of the fourth embodiment.

The ophthalmologic apparatus 1 includes the examination optical system, the optical system driver 2A (drive part), the anterior eye cameras 300 (two or more imaging parts), the analyzer 231, and a notification part. The examination optical system is an optical system for examining the eye E. The optical system driver 2A moves the examination optical system. The anterior eye cameras 300 substantially simultaneously photograph the anterior eye segment Ea of the eye E from different directions. The analyzer 231 analyzes photographic images captured by the anterior eye cameras 300 to obtain the three-dimensional position of the eye E. In addition, by analyzing the photographic images captured by the anterior eye cameras 300, the analyzer 231 determines whether the eye E is blinking. The notification part provides a notification on the result of determination by the analyzer 231.

Described below is a configuration example of the notification part. The notification part includes the display 240A and the controller 210. When the analyzer 231 determines that the eye E is blinking, the controller 210 displays warning information on the display 240A. Note that the notification mode is not limited to this. For example, not only such visual information, but audio information may also be output for notification.

<Modification>

The embodiments described above are mere examples for implementing the present invention, and therefore susceptible to several modifications and variations (omission, substitution, addition, etc.), all coming within the scope of the invention.

The anterior eye cameras 300 (imaging part) may be arranged below (−y direction) the lens center of the objective lens 22. With this, it is possible to reduce the possibility that the eyelid and eyelashes of a subject are caught in photographic images captured by the anterior eye cameras 300 (imaging part). Further, even if the subject has deep eye depressions (eye socket), the anterior eye segment can be suitably photographed.

The various features of the above embodiments may be combined in various ways.

In the above embodiments, two photographic images captured substantially simultaneously by the anterior eye cameras 300A and 300B may be synthesized by the image processor 230, and a composite image thus obtained may be displayed. This enables the observation of the three-dimensional form of the anterior eye segment Ea. The analysis process of the above embodiments may be performed by using the composite image.

In the above embodiment, the controller 210 is capable of displaying at least one of two photographic images captured substantially simultaneously by the anterior eye cameras 300A and 300B. This enables the observation of the morphology of the anterior eye segment Ea from different viewpoints (photographing positions).

The anterior eye cameras 300 may be mounted on the front surface of the case 420, or may be housed in the case 420. That is, the anterior eye cameras 300 may be arranged to protrude from the front surface of the case 420, or may be arranged substantially in the same surface as the front surface of the case 420. Incidentally, the anterior eye cameras 300 may be arranged such that the front surface thereof is located at a position that is recessed relative to the front surface of the case 420.

When the anterior eye cameras 300A are arranged not to protrude from the front surface of the case 420, there are such advantages that they do not interfere eyelid opening, external fixation operation, and the like, and a failure of automatic alignment due to vignetting of an image itself can be avoided.

The anterior eye cameras 300 may also be arranged in a position other than the front surface of the case 420. For example, the anterior eye cameras 300 may be arranged on the side surface of the case 420, and an optical system (mirrors, etc.) may be provided for changing the directions of the optical axes of the anterior eye cameras 300 to guide them to the eye E. Together with providing the anterior eye cameras 300 in the case 420, the same optical system may also be provided. If there is such an optical system, in view of the disturbance to the photography of the anterior eye segment, it may be desirable to provide the anterior eye cameras 300 and the optical system in the case 420. In this case, to avoid the influence of other optical systems (the examination optical system, etc.) on the photography of the anterior eye segment, it may be desirable to separate the anterior eye cameras 300 and the optical system from the other optical systems. Note that such separation of the optical systems may be achieved by using an optical path separating member such as a prism or a dichroic mirror.

In the above embodiments, the difference in optical path length between the optical path of the signal light LS and that of the reference light LR is varied by changing the position of the optical path length changing part 41; however, the method for changing the difference in optical path length is not limited to this. For example, a reflection mirror (reference mirror) may be arranged on the optical path of the reference light to change the optical path length of the reference light by moving the reference mirror along the traveling direction of the reference light, thereby changing the difference in optical path length. Besides, the optical path length of the signal light LS may also be changed by moving the fundus camera unit 2 and/or the OCT unit 100 relative to the eye E, thereby changing the difference in optical path length.

A computer program for realizing the aforementioned embodiments may be stored in an arbitrary recording medium that is readable by a computer. Examples of the recording medium include a semiconductor memory, an optical disk, a magneto-optical disk (CD-ROM, DVD-RAM, DVD-ROM, MO, etc.), a magnetic storage medium (a hard disk, a floppy (registered trade mark) disk, ZIP, etc.), and the like.

The program may be sent/received through a network such as the Internet or LAN.

What is claimed is:

1. An ophthalmologic apparatus comprising:
    an examination optical system configured for examining an eye;
    a drive part configured to move the examination optical system;
    two or more imaging parts configured to substantially simultaneously photograph an anterior segment of the eye from different directions;
    an analyzer configured to analyze photographic images captured by the two or more imaging parts to obtain a three-dimensional position of the eye, and displacement information indicating displacement direction and displacement amount of the eye due to eye movement, the analyzer including,
        a characteristic region specifying part configured to analyze the photographic images to specify a characteristic region in the photographic images corresponding to a characteristic site of the anterior segment,
        a shape information acquisition part configured to analyze the characteristic region to acquire shape information of the characteristic region, and
        a displacement information acquisition part configured to acquire the displacement information based on the shape information; and
    a controller configured to perform a first alignment process of controlling the drive part based on the three-dimensional position to move the examination optical system and a second alignment process of controlling the drive part based on the displacement information to move the examination optical system, wherein
    the characteristic region specifying part is configured to specify a pupil region corresponding to a pupil or an iris region corresponding to an iris as the characteristic region,
    the shape information acquisition part is configured to obtain an ellipse approximating a contour of the pupil region or the iris region, and calculate a major axis and a minor axis of the ellipse to acquire the shape information, and
    the displacement information acquisition part is configured to obtain the displacement direction based on direction of the major axis or the minor axis and the displacement amount based on a ratio of the major axis and the minor axis to acquire the displacement information.

2. The ophthalmologic apparatus of claim 1, wherein the analyzer includes
    a characteristic point specifying part configured to analyze two or more photographic images captured substantially simultaneously by the two or more imaging parts to specify a position in the photographic images corresponding to a characteristic point of the anterior segment, and
    a three-dimensional position calculating part configured to calculate a three-dimensional position of the characteristic point based on the position corresponding to the characteristic point specified, and positions of the two or more imaging parts, wherein
    the three-dimensional position of the characteristic point is used as the three-dimensional position of the eye.

3. The ophthalmologic apparatus of claim 1, wherein the controller is configured to perform the second alignment process after the first alignment process.

4. The ophthalmologic apparatus of claim 1, further comprising:
    an alignment optical system configured to project an alignment indicator for performing alignment of the examination optical system with the eye on the anterior segment; and
    a front image acquisition part configured to photograph the eye on which the alignment indicator is being projected to capture a front image of the anterior segment, wherein
    the analyzer is configured to analyze the front image to obtain displacement of the examination optical system with respect to the eye, and
    the controller is configured to determine whether the first alignment process has succeeded or failed, wherein, having determined that the first alignment process has failed, the controller performs the second alignment process after performing alignment by controlling the drive part based on the displacement of the examination optical system.

5. The ophthalmologic apparatus of claim 1, wherein the controller includes
    a first storage configured to store, in advance, first correspondence information in which movement direction and movement amount of the examination optical system are associated with the displacement direction and the displacement amount of the eye, and
    a first movement information specifying part configured to specify movement direction and movement amount corresponding to the displacement direction and the displacement amount indicated by the displacement information obtained by the analyzer based on the first correspondence information, and
    the controller is configured to perform the second alignment process based on the movement direction and the movement amount specified.

6. The ophthalmologic apparatus of claim 5, wherein the movement direction is perpendicular to an optical axis of the examination optical system.

7. An ophthalmologic apparatus comprising:
    an examination optical system configured for examining an eye;
    a drive part configured to move the examination optical system;

two or more imaging parts configured to substantially simultaneously photograph an anterior segment of the eye from different directions;

an analyzer configured to analyze photographic images captured by the two or more imaging parts to obtain a three-dimensional position of the eye, and displacement information indicating displacement direction and displacement amount of the eye due to eye movement; and a controller configured to perform a first alignment process of controlling the drive part based on the three-dimensional position to move the examination optical system and a second alignment process of controlling the drive part based on the displacement information to move the examination optical system, the controller including, a first storage configured to store, in advance, first correspondence information in which movement direction and movement amount of the examination optical system are associated with the displacement direction and the displacement amount of the eye, and a first movement information specifying part configured to specify movement direction and movement amount corresponding to the displacement direction and the displacement amount indicated by the displacement information obtained by the analyzer based on the first correspondence information, and the controller is configured to perform the second alignment process based on the movement direction and the movement amount specified, wherein the movement direction is perpendicular to an optical axis of the examination optical system, and the controller is configured to perform a third alignment process of controlling the drive part based on the movement amount to move the examination optical system in direction of the optical axis.

8. The ophthalmologic apparatus of claim 1, wherein the displacement direction includes cycloduction direction of the eye, and
the displacement amount includes a cycloduction amount of the eye.

9. An ophthalmologic apparatus comprising:
an examination optical system configured for examining an eye;
a drive part configured to move the examination optical system;
a fixation optical system configured to project a fixation target for visual guidance onto the eye;
two or more imaging parts configured to substantially simultaneously photograph an anterior segment of the eye from different directions;
an analyzer configured to analyze photographic images captured by the two or more imaging parts to obtain a three-dimensional position of the eye; and
a controller configured to perform a process of controlling the fixation optical system to change a projection position of the fixation target, a first alignment process of controlling the drive part based on the three-dimensional position to move the examination optical system, and a second alignment process of controlling the drive part based on the projection position of the fixation target to move the examination optical system, the controller including,
a second storage configured to store, in advance, second correspondence information in which movement direction and movement amount of the examination optical system are associated with the projection position of the fixation target, and a second movement information specifying part configured to specify movement direction and movement amount corresponding to the projection position of the fixation target projected by the fixation optical system based on the second correspondence information, and the controller is configured to perform the second alignment process based on the movement direction and the movement amount specified, wherein the movement direction is perpendicular to an optical axis of the examination optical system, and the controller is configured to perform a third alignment process of controlling the drive part based on the movement amount to move the examination optical system in direction of the optical axis.

10. The ophthalmologic apparatus of claim 9, wherein the fixation optical system includes
a fixation target presenting part configured to be capable of presenting the fixation target at a plurality of positions, and
a fixation target projection optical system configured to project the fixation target presented onto the eye, wherein
in the second correspondence information, the movement direction and the movement amount are associated with each of the plurality of positions,
the controller is configured to control the fixation target presenting part to present the fixation target in one of the plurality of positions, and
the second movement information specifying part is configured to specify the movement direction and the movement amount corresponding to a position where the fixation target is presented by the controller based on the second correspondence information.

11. The ophthalmologic apparatus of claim 9, wherein the controller is configured to perform the second alignment process after the first alignment process.

12. The ophthalmologic apparatus of claim 9, further comprising:
an alignment optical system configured to project an alignment indicator for performing alignment of the examination optical system with the eye on the anterior segment; and
a front image acquisition part configured to photograph the eye on which the alignment indicator is being projected to capture a front image of the anterior segment, wherein
the analyzer is configured to analyze the front image to obtain displacement of the examination optical system with respect to the eye, and
the controller is configured to determine whether the first alignment process has succeeded or failed, wherein, having determined that the first alignment process has failed, the controller performs the second alignment process after performing alignment by controlling the drive part based on the displacement of the examination optical system.

13. An ophthalmologic apparatus comprising:
an optical system including an examination optical system configured for examining an eye;
a drive part configured to move the examination optical system;
two or more imaging parts configured to substantially simultaneously photograph an anterior segment of the eye from different directions;

an analyzer configured to analyze photographic images captured by the two or more imaging parts to obtain a three-dimensional position of the eye, and pupil information indicating a state of a pupil; and a controller configured to perform an alignment process of controlling the drive part based on the three-dimensional position to move the examination optical system and an optical system control process of controlling the optical system based on the pupil information, wherein the optical system includes a fixation optical system configured to project a fixation target for visual guidance on the eye, the analyzer is configured to acquire pupil size as the pupil information, and the controller is configured to control the fixation optical system based on the pupil size to change intensity of a light flux projecting the fixation target as the optical system control process.

14. An ophthalmologic apparatus comprising:

an optical system including an examination optical system configured for examining an eye;

a drive part configured to move the examination optical system;

two or more imaging parts configured to substantially simultaneously photograph an anterior segment of the eye from different directions;

an analyzer configured to analyze photographic images captured by the two or more imaging parts to obtain a three-dimensional position of the eye, and pupil information indicating a state of a pupil; and a controller configured to perform an alignment process of controlling the drive part based on the three-dimensional position to move the examination optical system and an optical system control process of controlling the optical system based on the pupil information, wherein the optical system includes a first illumination optical system that is arranged coaxially with the examination optical system and configured to irradiate the eye with continuous light, and a first imaging optical system that is arranged coaxially with the examination optical system and configured to capture a moving image of the eye irradiated by the continuous light, the analyzer is configured to acquire pupil size as the pupil information, and the controller is configured to control the first illumination optical system based on the pupil size to change intensity of the continuous light as the optical system control process.

15. An ophthalmologic apparatus comprising:

an optical system including an examination optical system configured for examining an eye;

a drive part configured to move the examination optical system;

two or more imaging parts configured to substantially simultaneously photograph an anterior segment of the eye from different directions;

an analyzer configured to analyze photographic images captured by the two or more imaging parts to obtain a three-dimensional position of the eye, and pupil information indicating a state of a pupil; and a controller configured to perform an alignment process of controlling the drive part based on the three-dimensional position to move the examination optical system and an optical system control process of controlling the optical system based on the pupil information, wherein the optical system includes a second illumination optical system that is arranged coaxially with the examination optical system and configured to irradiate the eye with flash light, and a second imaging optical system that is arranged coaxially with the examination optical system and configured to capture an image of the eye in synchronization with irradiation of the flash light, the analyzer is configured to acquire pupil size as the pupil information, and the controller is configured to control the second illumination optical system based on the pupil size to change intensity of the flash light as the optical system control process.

16. An ophthalmologic apparatus comprising:

an optical system including an examination optical system configured for examining an eye;

a drive part configured to move the examination optical system;

two or more imaging parts configured to substantially simultaneously photograph an anterior segment of the eye from different directions;

an analyzer configured to analyze photographic images captured by the two or more imaging parts to obtain a three-dimensional position of the eye, and pupil information indicating a state of a pupil; and a controller configured to perform an alignment process of controlling the drive part based on the three-dimensional position to move the examination optical system and an optical system control process of controlling the optical system based on the pupil information, wherein the optical system includes a third illumination optical system that is arranged coaxially with the examination optical system, includes two or more diaphragms with different aperture sizes, and configured to irradiate the eye with illumination light, and a third imaging optical system that is arranged coaxially with the examination optical system and configured to capture an image of the eye irradiated by the illumination light, the analyzer is configured to acquire pupil size as the pupil information, and the controller is configured to selectively place the two or more diaphragms on an optical path of the third illumination optical system based on the pupil size as the optical system control process.

17. An ophthalmologic apparatus comprising:

an optical system including an examination optical system configured for examining an eye;

a drive part configured to move the examination optical system;

two or more imaging parts configured to substantially simultaneously photograph an anterior segment of the eye from different directions;

an analyzer configured to analyze photographic images captured by the two or more imaging parts to obtain a three-dimensional position of the eye, and pupil information indicating a state of a pupil; and a controller configured to perform an alignment process of controlling the drive part based on the three-dimensional position to move the examination optical system and an optical system control process of controlling the optical system based on the pupil information, wherein the analyzer is configured to acquire a pupil shape as the pupil information, and the controller is configured to control the drive part based on the pupil shape to move the examination optical system as the optical system control process.

\* \* \* \* \*